United States Patent
Schmelig et al.

(10) Patent No.: US 11,127,220 B2
(45) Date of Patent: Sep. 21, 2021

(54) METHOD FOR VIRTUALLY CONFIGURING A PIECE OF EQUIPMENT, COMPUTER PROGRAM PRODUCT AND CORRESPONDING AUGMENTED REALITY SYSTEM

(71) Applicant: Sartorius Stedim Biotech GmbH, Göttingen (DE)

(72) Inventors: Christian Schmelig, Körle (DE); Stefan Schlack, Göttingen (DE)

(*) Notice: Subject to any disclaimer, the term of this patent is extended or adjusted under 35 U.S.C. 154(b) by 0 days.

(21) Appl. No.: 16/760,421

(22) PCT Filed: Oct. 10, 2018

(86) PCT No.: PCT/EP2018/077534
§ 371 (c)(1),
(2) Date: Apr. 29, 2020

(87) PCT Pub. No.: WO2019/086214
PCT Pub. Date: May 9, 2019

(65) Prior Publication Data
US 2020/0342672 A1  Oct. 29, 2020

(30) Foreign Application Priority Data
Oct. 30, 2017  (DE) .................. 10 2017 010 190.6

(51) Int. Cl.
*G06T 19/00*  (2011.01)
(52) U.S. Cl.
CPC .................. *G06T 19/006* (2013.01)

(58) Field of Classification Search
None
See application file for complete search history.

(56) References Cited

U.S. PATENT DOCUMENTS

| | | | |
|---|---|---|---|
| 2007/0156540 A1 | 7/2007 | Koren et al. | |
| 2015/0265369 A1* | 9/2015 | Garbey ................. | A61B 17/34 600/410 |
| 2017/0076500 A1 | 3/2017 | Maggiore et al. | |

FOREIGN PATENT DOCUMENTS

| | | |
|---|---|---|
| EP | 3 165 979 A1 | 5/2017 |
| WO | WO 2015/075705 A2 | 5/2015 |

OTHER PUBLICATIONS

International Search Report and Written Opinion, dated Jan. 23, 2019, issued for International Application No. PCT/EP2018/077534, 14 pages (with English translation).

* cited by examiner

*Primary Examiner* — Robert J Craddock
(74) *Attorney, Agent, or Firm* — Klarquist Sparkman, LLP

(57) ABSTRACT

A method for virtually configuring a piece of equipment comprises providing an augmented reality system having a computer unit and at least one sensor unit, detecting a sensor dataset associated with a physical environment by means of the at least one sensor unit, determining a virtual environment based on the sensor dataset by means of the computer unit, and determining a virtual arrangement of at least one virtual and/or physical equipment element relative to the virtual environment.

19 Claims, 14 Drawing Sheets

Figure 1a

Virtual Configuration of a Piece of Equipment ~100

Provision of an augmented reality system 1000:
- A computer unit 10;
- A sensor unit 20 ((3D enabled) camera, unit for using photogrammetry and recording 3D coordinates, 3D data acquisition and object reconstruction, laser scanner, infrared camera, chronometer, etc.;
- Screen 11, computer screen, touch screen of a smartphone/tablet 12, etc.;
- Identity marking 62 and/or Object marking and/or spatial marking

↓ ~110

Receiving a sensor dataset 200 of a physical environment 30:
Sensor dataset 200: 3D coordinates, temperature, E fields, vibration, light intensity, etc.;
Physical surroundings 30/real rooms: Laboratory, hall, etc.

↓ ~120

Determining/simulating/mapping a virtual environment 40:
- Object reconstruction/generating/reconstructing a 3D/spatially temporal model;
- Generating field maps/overlaying sensor data with a 3D/spatially temporal model.

↓ ~130

Determining a virtual arrangement-selection of the elements 50: ~132

~131

| Providing a selection 57 of virtual equipment elements 50, in particular compatible with each other; <br><br> - Selecting at least one virtual equipment element 50. | and/or | - Providing a registered physical equipment element 51 in the physical environment 30;<br>- Identifying the registered physical equipment element 51 with a virtual equipment element by means of contour/shape feature and/or identity marking 62;<br>- Assigning the registered physical equipment element 51 to the virtual equipment element 50 with parameter dataset 300 corresponds to selecting the virtual equipment element 50. |

↓

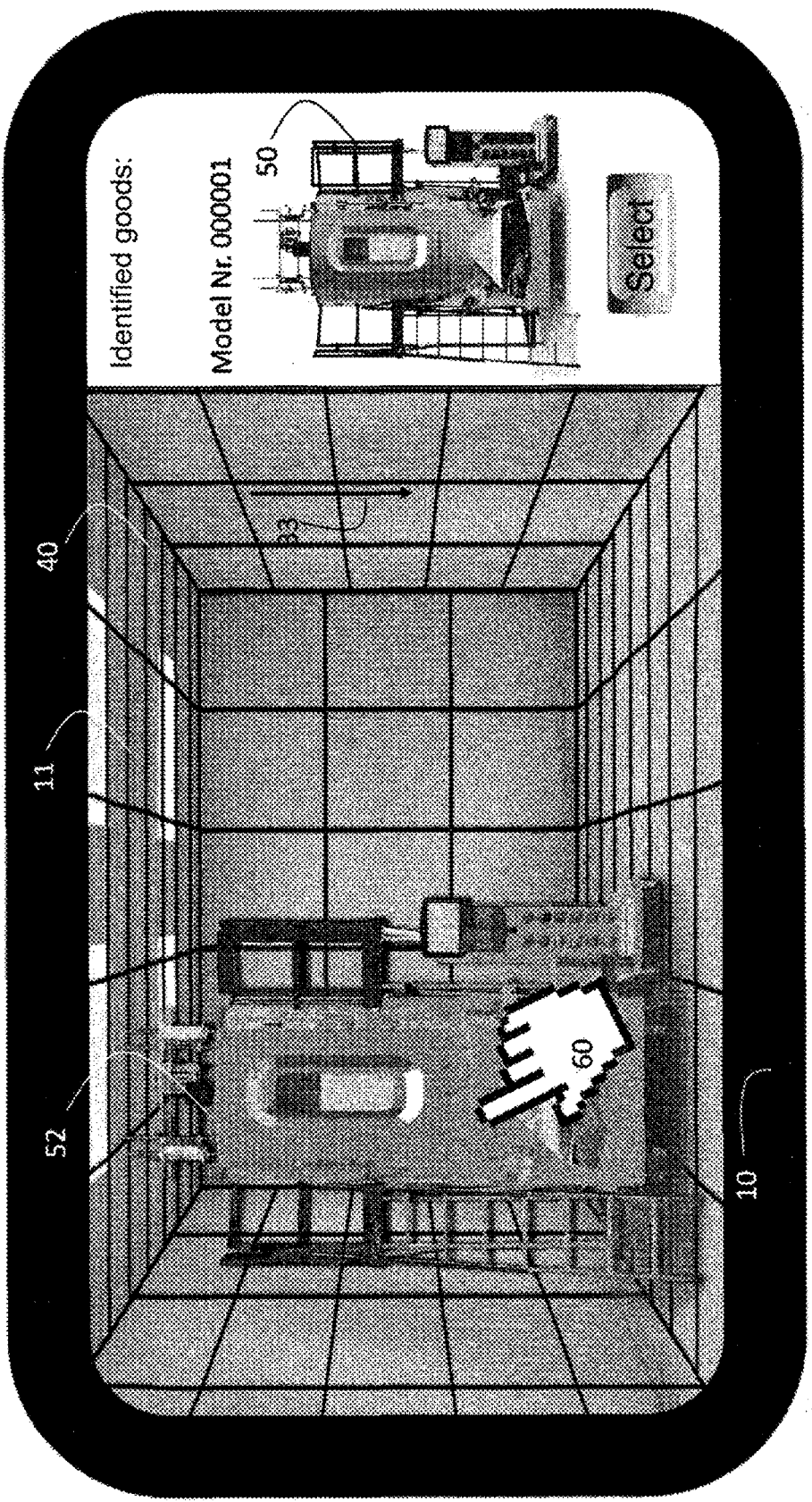
Figure 3   Steps 130-140/132-142

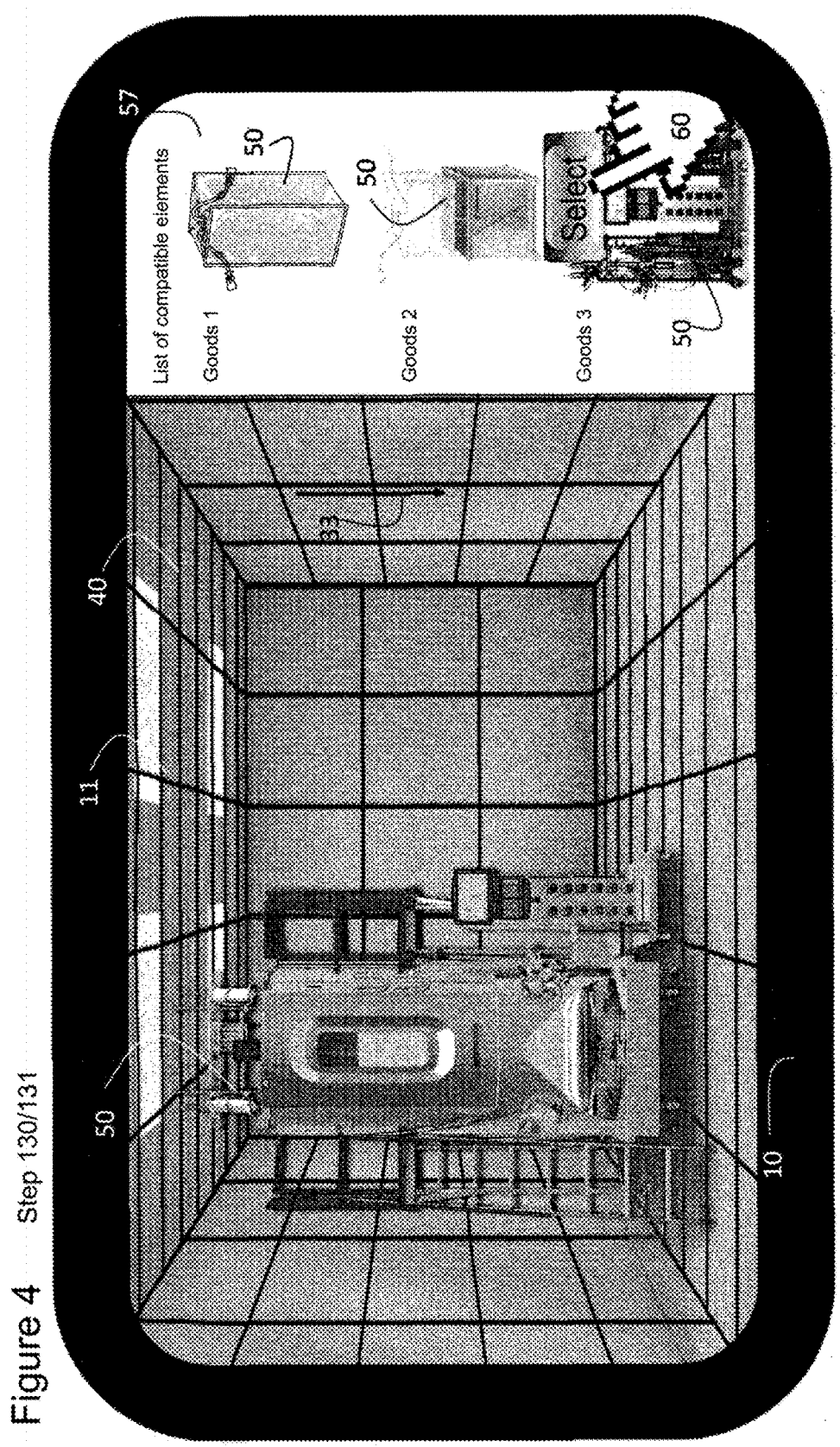
Figure 4 — Step 130/131

Figure 7 Step 140/141

Figure 8 Step 150

METHOD FOR VIRTUALLY CONFIGURING A PIECE OF EQUIPMENT, COMPUTER PROGRAM PRODUCT AND CORRESPONDING AUGMENTED REALITY SYSTEM

CROSS REFERENCE TO RELATED APPLICATIONS

This is the U.S. National Stage of International Application No. PCT/EP2018/077534 filed Oct. 10, 2018, which in turn claims the benefit of German Patent Application No. 10 2017 010 190.6, filed Oct. 30, 2017. The prior application is incorporated herein by reference in its entirety.

DESCRIPTION

The present invention relates to a method for virtually configuring a piece of equipment, computer program product and corresponding augmented reality system. In particular, an improved method is provided for configuring and/or adapting and/or individualizing and/or optimizing a piece of equipment, in particular bioprocessing equipment. The invention can be used in particular in the following fields: Biotechnology, biopharmaceutical and pharmaceutical industries, medical technology, chemical industry, physical technology, food technology, processing technology and the like. The interactive use of the method by a user, in particular a customer who wishes to place an order via a self-configured piece of equipment for supplier/seller, for example online, is particularly preferred.

To date, it is common practice for a piece of equipment to be configured by positioning and/or constructing and/or assembling and/or sampling and/or operating real equipment elements in a real environment. To this end, the operating status and/or the functionality and in particular the correct connection of the real device elements to be mounted are checked visually and/or manually. Prior to commissioning the equipment, a user must check all compatibilities and/or ports accordingly, including in particular technical data sheets and the selection of suitable and compatible real equipment elements.

With increasing complexity of systems and pieces of equipment, more effective and in particular more efficient methods for configuration and/or optimization and/or for test runs are required. In particular, the biopharmaceutical industry, which is subject to strict regulations and record keeping requirements, relies on largely reliable and trouble-free operation of installations and equipment. Moreover, usually very high-quality products produced and/or used within a piece of equipment, for example in single-use containers of a bioreactor, require properly functioning equipment elements and/or the proper interaction of a plurality of equipment elements. This presupposes that erroneous mounting is already avoided in the course of configuring a piece of equipment.

The invention is therefore based on the object of providing a method, a computer program product and an augmented reality system, each enabling an efficient configuration of a piece of equipment.

The object is achieved by the independent claims. In particular, preferred embodiments are the subject-matter of the dependent claims.

The invention relates to a method for virtually configuring a piece of equipment, in particular bioprocessing equipment, wherein the method comprises the following steps:

providing an augmented reality system or a system for generating an augmented reality: comprising: a computer unit and at least one sensor unit;
detecting a sensor data set associated with a physical or real environment by means of at least one sensor unit;
determining a virtual environment based on the sensor dataset by means of the computer unit;
determining a virtual arrangement of at least one virtual equipment element and/or an image of a physical equipment element relative to the virtual environment, wherein the virtual and/or physical equipment element is assigned a respective parameter dataset; and
generating a prediction or predicting, in particular simulating a functionality and/or an operating status of at least a part of the equipment based on the parameter dataset and the sensor dataset.

The invention also relates to a method for virtually configuring a piece of equipment, in particular bioprocessing equipment, wherein the method comprises the following steps:

providing an augmented reality system or a system for generating an augmented reality: comprising: a computer unit and at least one sensor unit;
detecting a sensor data set associated with a physical environment by means of at least one sensor unit;
determining a virtual environment based on the sensor dataset by means of the computer unit;
determining a virtual arrangement of at least one virtual equipment element relative to the virtual environment, wherein the virtual and/or physical equipment element is assigned a respective parameter dataset; and
generating a prediction, in particular simulating a functionality and/or an operating status of at least a part of the equipment based on the parameter dataset and the sensor dataset.

Bioprocessing equipment is understood to mean objects/elements, in particular for processing biological media and also their systemic combination, for example in modular form and in systems. Such a system and/or element can be or comprise, for example, a bioreactor, a disposable bag, a container, a tank, a filter system, a mixing tank, a fermentation tank, etc., which can be arranged as individual objects or in so-called process units (unit operations). These can be accommodated in premises, such as laboratories, clean rooms, manufacturing and production halls, where, for example, biopharmaceutical substances and/or functional food are developed and produced. The invention can be used in particular in the pharmaceutical and/or biopharmaceutical industry and/or in the food and/or beverage industry.

A medium can in particular be a gas and/or a liquid and/or a solid, for example a granulate. In particular, the term "medium" may be understood to mean a dispersion, in particular an emulsion, a suspension, a gel and/or a foam. A medium particularly preferably comprises a biological and/or chemical substance, for example cells, plants, bacteria and/or the constituents and/or products thereof. For example, a medium may be a cell culture medium and/or a buffer system. The medium is most preferably a fluid or the medium has fluid properties. A medium may further comprise a substance or substance mixture which is used in the production and/or as a component of food, in particular a so-called functional food. In other words, a medium may in particular be any substance or anything that can flow.

In particular, the following method is carried out based on an augmented reality system or a system for generating an augmented reality comprising a computer or a computer unit and at least one sensor or detector unit:

recording sensor data by means of the sensor unit or entries of a sensor dataset corresponding to a physical environment or at least partially characterizing a physical environment;

translating, transforming or digitalizing the physical environment into a virtual environment based on entries of the sensor dataset, in particular comprising a reconstruction and/or mapping of the physical environment into a virtual format;

virtual arrangement or positioning of virtual equipment element assigned to entries of a parameter dataset within and/or with respect to the virtual environment;

virtual testing, in particular comparing and/or simulating equipment and its function based on the entries of the parameter dataset and the sensor dataset.

This advantageously enables a method which translates and/or digitizes a real physical environment and preferably a physical equipment element into a virtual depiction or a virtual environment. In other words, physical aspects of a real environment are digitized or recorded digitally. Virtual equipment elements can be virtually added to the virtual environment. In particular, a virtual equipment element is substantially a model in its virtual properties, at least one approximate model of a real physical device element or corresponds at least partially in its virtual properties to the properties of a real physical equipment element.

The virtual properties of a virtual equipment element are defined by characteristic data which can typically be taken, among other things, from corresponding data sheets and/or a property database. Such characteristic data can be or comprise a component of a parameter data set. This also corresponds to a manner of digitizing and/or modeling a physical equipment element. Thus, a virtual environment comprising virtual device elements corresponds to a digital model of a real physical environment comprising one or more physical equipment elements. The model may be arbitrarily detailed, that is to say, it can be characterized by any number of parameters determined, among other things, by the physical environment.

The user is thus advantageously enabled to configure virtual equipment, in particular bioprocessing equipment or, for example, a laboratory set-up for biotechnological applications in a particularly efficient and intuitive and in particular interactive computer-supported manner. The virtual equipment comprises at least one virtual equipment element. Configuration is done essentially before the physical equipment element corresponding to at least one virtual equipment element is installed, wherein it has to be frequently ordered and actually procured.

In this manner, a user of the method interested in installing one or more corresponding equipment elements can try and test them in advance as to whether they meets their requirements and/or whether they are compatible with other, in particular, already existing physical equipment elements. Preferably, the user can check and/or test and/or try to determine whether the equipment can be operated substantially without error.

The described method is particularly advantageous for configuring complex devices and systems or pieces of equipment which are defined by a plurality of parameters of a parameter dataset. Accordingly, it is not necessary to actually install said equipment or system in order to test or try it out it in the physical environment. The device or the equipment is virtually tested or tried out in augmented reality in any complex embodiment, including any number of parameters, and predicts in particular whether the correct error-free function is given or not. In other words, it is already possible to virtually find out or predict whether a piece of equipment, such as is desired or initially configured by a user, can be constructed and/or connected and/or set up and/or operated without error. In this case, it is particularly preferred to be able to simulate a function or functionality and/or an operating status, so that the user also receives information on whether the desired configuration has the functionality suitable for its purposes and claims.

A function may, for example, comprise process steps which are carried out by an element or the entire equipment, and may in particular comprise temperature control, mixing of the medium, addition of a substance to the medium, pressure build-up or reduction, draining of part of the medium and/or other steps. An operating status may comprise the compatibility or "fitting together" of elements, the "fitting" of elements into the space and/or a specific status, such as "container empty" or "container full", "valve open", "valve closed", "element at operating temperature" or similar. A "function and/or functionality" may also not be clearly distinguishable from an "operational state", and therefore the terms "function and/or functionality" and "operation status" may mean the same thing.

The user and/or the distributor of physical equipment elements can thus minimize a considerable amount of cost and time by means of the described method by configuring complex equipment and/or systems in advance in a virtual, interactive and computer-supported manner or by avoiding corresponding configuration errors. In particular, installing (in particular manufacturing and assembling, purchasing and/or delivering) physical equipment elements such as biotechnological systems and/or bioreactors 'on suspicion' may be avoided, wherein there may be a risk that an erroneous function and/or compatibility, in particular in interaction with the physical environment and/or other physical equipment elements, is then determined on site after installation. In that case, the improper physical device element which has been procured or at least delivered would have to be returned, causing undesirable time and cost for the user and/or the supplier.

Moreover, it can advantageously be avoided that a customer and/or a user may have to study a plurality of complicated data sheets and/or catalogs and/or query databases in order to determine and select a suitable and compatible equipment element. The method described has the advantage of providing a particularly intuitive, efficient and application-friendly option for configuring a device.

In accordance with one aspect, at least one sensor unit comprises a camera or a photographic apparatus, in particular a 3D-capable camera, i.e. a camera, which is capable of detecting two- or three-dimensional coordinates of a room or an environment. In this case, the step of detecting the sensor data set associated with the physical environment may comprise a step of detecting an image of the physical environment. In particular, a sensor data set can comprise spatial information, in particular a 3D topography and/or three-dimensional (3D) coordinates of a room, and preferably a gravitational direction. In particular, a photograph is taken of a physical real environment, for example a laboratory. The photograph preferably comprises data containing three-dimensional coordinates or data from which three-dimensional coordinates can be derived. Such data correspond, for example, to entries of a sensor data record.

The detection of physical properties of a physical or real environment allows a virtual 3D environment to be reconstructed as an image of the physical environment. This is particularly advantageous for determining distances and for comparing dimensions. For example, it may be determined whether a device element has sufficient space at the desired destination. Physical components, for example parts of laboratory equipment and/or pieces of furniture, can also be recognized in particular as storage areas and can be considered for the virtual positioning or arrangement of virtual equipment elements.

The recording of a gravitational direction is particularly preferred, which can be given for example by a marking in space, referred to here as a gravitational marking. It is also conceivable to determine the direction of gravity by means of at least one gravitational sensor that is located in the physical environment and/or integrated in a detector (e.g. a smartphone). For example, using the direction of gravity indicated on the gravitational marking and the position of two virtual equipment elements, it is possible to predict, for example, what pumping power is required to generate a flow from one virtual equipment element to another virtual equipment element. In addition, load distributions and/or lengths of cables and tubes that are sagging or running or lying on the floor can be calculated.

In accordance with one aspect, the method further comprises a step of providing at least one room or environmental marking, in particular comprising a first augmented reality mark (briefly: AR marking) and/or a QR marking (in particular according to ISO/IEC 18004:2006) in the physical or real environment, wherein the spatial information, in particular a 3D topology of the physical environment, can be detected and reproduced or specified by means of the spatial marking.

An augmented reality (AR) marking can be substantially any type of marking that enables classification or identification. For example, a sheet of paper having a dot or cross thereon may serve as a physical marking. The user can place the sheet of paper at a location in the physical environment, and the computer unit recognizes that a virtual equipment element is to be virtually arranged at the location. For example, gravitational direction can also be indicated by such an AR marking, for example by an arrow. In essence, the function or coding of the AR marking only play a role. The AR marking itself can be any possible marking that can be arranged in a detectable manner (in particular, in a visible manner) in the physical environment.

An AR marking can be represented not only on its own, but also, for example, together with a QR marking or comprise such a mark. In general, a distinction must be made between the coding of a QR marking and the coding of an AR marking, since the QR marking in the form of black and white boxes substantially corresponds to or is assigned to a determined string in accordance with the corresponding QR coding, which can be read out by a computer unit that knows the QR coding. The QR marking contains substantially no encoded information about a position and/or orientation of an object in space due to the QR coding. However, since an AR marking may have any pattern, it could also be represented in the form of a QR marking. In order to analyze the spatial information, only the pattern itself would then be analyzed on the basis of the perspective depiction or on the basis of its position in space, wherein the QR coding can initially be disregarded. However, in order to read out the coded information, for example an identity of the object to be displayed, the CD coding is decrypted. Both can take place separately. Thus, in principle, a QR coding could also serve as AR marking.

Providing or applying a spatial marking in a room allows the user who does not own and/or does not want to use a 3D camera to advantageously mark or indicate the spatial information of a surface in space in a simple manner, so that a computer unit can extract the spatial information therefrom. Such spatial markings can for example be provided online by the distributor of the equipment elements for printing. A suitable algorithm can then be executed by the arithmetic unit, whereby the spatial coordinates or features of the marked area are derived or determined.

In accordance with one aspect, the method further comprises a step of providing an object marking (which may also be referred to as a destination mark of a virtual and/or physical equipment element and may optionally also comprise an identity marking), in particular comprising a second augmented reality mark (briefly: AR marking) and/or a QR marking (in particular according to ISO/IEC 18004:2006) in the physical environment, wherein a virtual position or a virtual destination and/or a virtual orientation with respect to the virtual environment and/or an identity of the virtual equipment element is given or specified by means of the object marking.

An object marking may be a marking that a user places in the physical environment at a physical destination where a virtual equipment element is to be located at the destination in the virtual environment. The object marking can comprise information about the destination and/or about the orientation of the virtual equipment element relative to the virtual environment and/or about the identity of the virtual equipment element.

The object marking particularly preferably comprises an AR marking, which in particular comprises information about its position and location in the space of the physical environment. This information is then translated in such a way that a virtual equipment element can be arranged in a virtual space on the basis of the AR marking and its location or position in the space of the physical environment. In particular, the AR marking also contains information about the identity of the virtual equipment element, so that the computer unit can identify the virtual equipment element and arrange it virtually in the virtual environment accordingly. This specific case could be given by physically placing an AR marking and a QR marking at a location in the physical environment. A very special case is given when only one QR marking is physically arranged, which is then read out on the basis of the position of its pattern in space with respect to the spatial arrangement and is read out by means of decrypting the QR coding for its coded content, for example comprising an identity.

In accordance with one aspect, the method comprises the following steps:
  allowing a selection by a user and/or the computer unit of at least one virtual equipment element, preferably from a selection of several virtual equipment elements, for example from a product range or a product catalog; and in particular
  providing a registered or known physical equipment element in the physical environment, wherein at least one virtual equipment element is preferably selected by means of the computer unit, in particular automatically, and wherein at least one virtual equipment element is selected based on a step of identifying the registered physical equipment element with a virtual equipment element, in particular based on the selection of the plurality of virtual equipment elements.

In other words, the user can select a desired virtual equipment element, in particular from a selection, for example from an online product catalog itself. Additionally or alternatively, a computer unit can also select a suitable, for example, compatible virtual equipment element. In particular, a computer unit can propose a plurality of suitable virtual equipment elements from which the user can choose and/or select a virtual equipment element. In particular, a computer unit can recognize a registered physical device element positioned in the physical environment and assign it to a respective virtual device element corresponding to an automatic selection of the virtual equipment element predetermined by the equipment element present in the physical environment.

The described selection of a virtual equipment element has the advantage of being particularly intuitive, efficient and user-friendly. The computer unit can assist the user in selecting a suitable or appropriate virtual equipment element, so that it is no longer necessary to look at a data sheet. The computer unit can also recognize automatically registered devices, i.e. registered physical equipment elements, which are sold by the distributor and/or which have been sold in the past.

In accordance with one aspect, the above-described step of identifying the registered physical equipment element comprises a step of recognizing one or more shape features of the equipment element and/or an identity marking, in particular a third AR marking and/or QR marking of the registered physical equipment element.

The embodiment in which a computer unit recognizes which registered device or physical equipment element is involved on the basis of typical or characteristic shape features of physical equipment elements is particularly preferred, since advantageously substantially no input is required from the user. Another embodiment is based on providing an identity marking that the user can attach to the respective physical equipment element prior to detection by the sensor dataset. The computer unit evaluates this identity marking, which, for example, can be an AR marking, and assigns or allocates the respective virtual equipment element to the physical equipment element.

In accordance with one aspect, at least one virtual equipment element comprises at least one of the following equipment elements: a bioreactor, a disposable bag, a container, a tank, a filter system, a mixing device, a fermentation tank, a centrifuge, a chromatography column, a membrane adsorber, a filling device and/or the at least one virtual equipment element comprises at least one virtual connection element, in particular at least one of the following: a cap, an adapter, a connection, a connector, a hose, a pipe, a cable, a conduit, a tube, and a pump. The parameter dataset further comprises in particular at least one variable and/or a fixed value of the following parameters: identification coding, order number, volume, length, spatial extent, diameter, structure, material, operating range, operating limit, compatibility with a further virtual equipment element, compatibility with a biological and/or chemical reaction, parameter data set to a medium, in particular a fluid medium, and preferably the biological and/or chemical reaction of the medium.

Accessories for biotechnological and/or chemical applications, for example, among other things, bioreactors, reusable and/or disposable bags, containers, tanks, filter systems, mixing tanks and/or equipment, fermentation tanks, a centrifuge, a filtration column, a membrane adsorber, a filling device and/or the like, can have any complexity in their handling or operation. These are often very special devices and articles or an accessory that can be used for very specific purposes. It is therefore rarely obvious whether different devices are compatible with one another and can be coordinated or harmonized with one another. The accessory mentioned by way of example is distinguished in particular by the parameter entries of the respective parameter dataset.

To check whether two devices are compatible with each other, it is usually necessary to compare parameter entries. In accordance with the aspect mentioned above, this step can be (at least partially) automated, so that the computer unit evaluates or assesses or predicts in advance whether two devices are compatible. To this end, virtual equipment elements are generated, for example virtual bioreactors, virtual disposable bags, virtual containers, virtual tanks, virtual filter systems, virtual mixing tanks, virtual fermentation tanks which correspond to the respective physical equipment elements as virtual models.

By way of example, the virtual and/or physical equipment elements may be characterized by data and/or parameter entries, such as volume, material, compressive strength, spatial expansion, diameter, structure, operating range, operating limit, compatibility with another virtual equipment element, compatibility with a biological and/or chemical reaction, and/or a sterilization method.

The accessory often includes containers or the accessory comprises containers in which media, for example buffer systems and/or cell culture media, are processed and/or stored. It may happen that a medium is to flow between two containers, for example if a first process, e.g. the substance is processed in a medium in a first container and is then transferred to a second or to further containers for a second process. This assumes that a virtual connection element virtually connects both containers to one another, for example, among other things, through a virtual hose, a virtual pipe, a virtual line, a virtual pipe, a virtual pump, a virtual attachment, a virtual adapter, a virtual and/or physical connector and/or a virtual connection, if the medium is not to be transported elsewhere. In particular, each of the above elements corresponds to a real, that is to say, physical hose, pipe, line, tube, pump, attachment, adapter or connection. Thus, for example, it is also possible to predict, in particular simulate, whether or how a medium, in particular a liquid, is to be introduced between two containers. In particular, a required pumping power can also be determined, preferably taking into account the gravitational force or the gravitational direction. Moreover, it may be possible to predict, in particular simulate, a plurality of processes in a plurality of containers.

A virtual connection element may be, among other things, a virtual cable corresponding to a physical cable. For example, an outlet existing in the physical environment may be recognized by the computer unit and translated into a virtual outlet. In this case, a virtual equipment element, in particular a power-operated device, can be virtually connected to the virtual outlet by the virtual cable. It would also be possible to connect a plurality of virtual equipment elements to one another, for example by a virtual power cable and/or a virtual data cable.

A virtual equipment element is defined by the data and/or parameter entries of a parameter dataset. A virtual connection element, such as a virtual tube, can be defined, among other things, by the following data entries of a parameter dataset: volume, length, weight per unit length, diameter, structure, material, strength and/or flexibility, operating range with regard to temperature, acid and/or base concentration and/or pressure, corresponding operating limit, compatibility with another virtual equipment element, compatibility with a biological and/or chemical reaction, resistance to sterilization, and reactive/inert property with respect to substances.

A data and/or parameter entry may also comprise a function or a dependency. For example, a characteristic determined in the experiment may reproduce or depict a dependence between two values or data and/or parameter entries. For example, material strength and/or material expansion of a tube relative to pressure may be applied or described by the function.

The data entries may serve, for example, to simulate a flow of a medium and/or to predict which virtual adapter or which virtual connection piece is required.

Other data entries of the parameter dataset may relate to a medium and/or a process. Although such data entries do not characterize the intrinsic properties of an equipment element, they can serve to predict and in particular simulate a process and/or a flow of a medium. For example, parameters such as a viscosity and a density as well as the volume of the medium are required for determining a material flow. Using these parameter entries and the parameter entries of a virtual tube, such as the diameter and the length, it is possible to calculate how the medium will flow through the tube.

Other data entries which correspond to administrative values and characterize a virtual and thus also physical equipment element may be an identification coding, an order number, a price per piece or per meter and/or an existing piece number. These parameters may be used to determine a price offer.

Parameter entries may comprise fixed entries, that is to say by the user, in particular invariable values by a buyer. For example, this would be the case in the case of values or parameter entries, such as identification coding, order number, but also in the case of parameter entries, such as weight per volume or length unit, material strength and the like. Nevertheless, parameter entries may also be changed by a user and/or a buyer or customer. For example, the customer may determine the length of a connection element, the volume of a container or the material on a scale with continuous or discrete values.

In accordance with this aspect, a high degree of flexibility for configuring the equipment is made possible and at the same time a plurality of operating statuses may be predicted, in particular simulated. Therefore, this embodiment offers a particularly high degree of user-friendliness and efficiency.

In accordance with one aspect, determining the virtual arrangement comprises determining at least two virtual equipment elements, wherein an equipment element comprises a virtual connection element, and the method further comprises the steps of:
  checking the compatibility between at least two virtual equipment elements;
  wherein compatibility was found in the test:
    allowing virtual connection of at least two virtual equipment elements by means of the virtual connection element by the user and/or the computer unit;
  wherein compatibility was not detected in the test:
    issuing an error message reporting the lack of compatibility.

In particular, there is an advantage in being able to predict whether two physical equipment elements are compatible with each other so that this is not detected until the physical equipment elements have been acquired and delivered to the customer. Compatibility is tested by the virtual configuration of the virtual equipment elements. Compatibility may, for example, be opposed, among other things, if two connections were not compatible or if operating ranges would not overlap, for example with respect to pressure or temperature. By issuing an error message reporting the lack of compatibility, the users and/or customers can make a decision as to whether they actually want to acquire the physical equipment elements corresponding to the selected virtual equipment elements, or whether they prefer to select a compatible physical equipment element that meets their requirements. The computer unit may preferably make a selection of compatible equipment elements from which the user may find or select a suitable one.

If the test results in all virtual equipment elements are compatible with one another, the user and/or customer may be certain that he or she may order the desired equipment elements without the risk that these equipment elements will not be compatible with one another on site.

In accordance with an aspect, determining the virtual arrangement comprises determining at least three virtual equipment elements, wherein at least one of the three virtual equipment elements corresponds to the virtual connection element; wherein the parameter dataset corresponding to the virtual connection element comprises a length of the connection element; and wherein at least two of the three virtual equipment elements respectively comprise at least one port for connecting a respective end of the virtual connection element; and the method further comprises the following steps:
  determining a virtual distance between at least two ports in the virtual environment based on the sensor dataset, the parameter dataset, and the virtual arrangement;
  determining the virtual length of the connection element, in particular an optimal length, in particular based on the distance between at least two ports in the virtual environment, wherein determining the length is by means of a computer unit and/or by means of a user.

In accordance with one aspect, when the virtual length is being determined, the connection element is arranged in the virtual environment taking into consideration a detected gravitational direction and the resulting weight force.

The described embodiment has the advantage that a connection element, in particular a tube can be adapted to the equipment in an efficient and intuitive way, as well as to the virtual equipment elements and to the positioning of the equipment elements in the virtual environment. Thus an optimal length of a tube may be determined depending on its desired virtual course in the room and it can be avoided that a length that is too short or an excess "on suspicion" is selected. In particular, the course of a tube is determined realistically by its own weight force. Each of the two ends of the virtual tube is connected to two virtual equipment elements. The virtual tube depends on a virtual port of a virtual equipment element and extends virtually along the virtual ground to another virtual port of the other virtual equipment element.

In accordance with one aspect, the augmented reality system further comprising a screen, in particular a touch screen, and the method further comprising a step of imaging the virtual environment and at least one virtual device element in the form of an augmented reality image of the virtual arrangement on the screen.

In accordance with one embodiment, a user interface mapped on the screen is designed to be used interactively by the user. This means that the user can enter inputs which are processed by a computer unit. An embodiment in which the user interface is intuitive and simple is particularly preferred. In particular, the virtual environment, that is to say the reconstructed physical environment or the image of the physical environment, together with selected virtual equipment elements positioned in the virtual environment, are displayed on the screen within the user interface. The user can thus obtain a visual impression during the method steps of the virtual configuration of the configured equipment or its intermediate results.

In accordance with one aspect, determining the virtual arrangement further comprises the step of virtual arrangement, whereby the user uses the screen to drag and drop at least one virtual equipment element.

This preferred embodiment allows the user to particularly intuitively and efficiently position, shift, add, and/or modify virtual elements in a virtual environment, and to determine, modify, optimize, and/or change parameters or parameter entries of a parameter dataset, among other things. This can be done on the one hand by means of a mouse pointer or cursor and/or "drag and drop" and in particular the method step can be carried out manually on the touch screen. No particular expertize or prior knowledge is required for carrying out the step in accordance with this aspect, and the step can be carried out intuitively in a short time. Drag-and-drop is the process of selecting and virtually grabbing an item by clicking by means of the mouse pointer and then virtually dragging the item to a desired location in the user interface on the screen.

In accordance with one aspect, at least one variable set of the parameter data set, in particular a length of the virtual device element, can be determined by the user on the screen, in particular by actuation on the touch screen.

This particularly intuitive embodiment allows the user to determine and/or predict the possible course of a tube, for example, depending on the selected length. By means of a so-called "slider" or "track bar" the user can, for example, dynamically adjust or determine how long a virtual tube should be by means of a mouse pointer or by hand on the touch screen. Alternatively, a discrete value and/or parameter entry may be entered or clicked.

Parameter entries can be preferably set dynamically or selectively. In other words, the user can determine on a scale continuously or discretely what value a parameter entry of the parameter dataset should assume. For example, the user can determine by means of a "check box" or a slider whether the volume of a container is to assume, for example, discrete values, such as 5 l, approximately 100 l, approximately 200 l, approximately 500 l, approximately 1000 l, approximately 3000 l or approximately 5000 l. This makes the configuration particularly simple and efficient.

In accordance with one aspect, the sensor dataset associated with the physical environment comprises at least one of the following values: temperature, time, electric field strength, light intensity, vibration, and noise.

In other words, by means of the sensor or the sensor unit, it is preferably possible to record a value or an associated field, which can be overlaid, for example, with the spatial coordinates. If one of the sensor units is an infrared camera, the user can make a recording of the temperature of the room overlaid with the spatial depiction or the virtual environment. Based on such a data set, the influence of such a value as the temperature on an equipment element and/or a process running within an equipment element can be simulated. This special embodiment allows the user to simulate processes in advance on a relatively complex level, i.e. including a plurality of sensor parameters of a sensor parameter dataset, and to predict whether the selected virtual equipment elements meet the requirements of the physical environment and the desired processes in reality as physical equipment elements. Since the products used and/or produced in biochemical processes are often very high-grade media or substances, it is particularly advantageous if a process can be modeled at least approximately using the available parameters in such a way that the success or yield of a process can at least be estimated or predicted in advance, in particular simulated. In this way, it has been possible to avoid executing a real process with high cost with inappropriate physical equipment elements and/or parameters.

An embodiment of the method may also comprise a step of identifying disruptive factors, such as light and/or vibration, to alert the user that the disruptive factor may be problematic for the use of a physical equipment element or for the operation of a process and should be eliminated by the user.

In particular, sensor parameters are recorded dynamically over a certain period of time so that, for example, the effect of a temperature fluctuation on a process can be predicted.

In accordance with one aspect, the step of predicting the operating status of at least a part of the equipment comprises a step of simulating at least one dynamic value of a dynamic process, based on the sensor data set, the parameter dataset and/or the virtual arrangement. The dynamic process comprises in particular at least one of the following properties or processes: a material flow, a biological process, a chemical process, a physical process and/or a mechanical process. Parameter entries with regard to a desired process are therefore preferably also provided. For example, a user may indicate which amount(s) and/or which substance(s) are used for the process. For example, a starting temperature, a starting pressure and/or a stirring speed can also be set. The method may be adapted to predict the course of the process with respect to the biochemical and/or thermodynamic processes.

In accordance with one aspect, the step of predicting an operating status comprises a step of reporting a correct operating status or reporting an erroneous operating status based, in particular, on the step of simulating at least one dynamic condition.

In a model of the virtual equipment, which the user has configured in particular with the aid of a suitable user interface, it is advantageous to test or check in advance whether the corresponding physical equipment will satisfy the user's requirements. If this is not the case in accordance with the prediction and/or simulation, the user can easily or flexibly exchange virtual equipment elements and check whether the reconfigured virtual equipment achieves better results with regard to the dynamic processes. Alternatively or additionally, the user can also adapt or change or vary parameters of a parameter dataset.

Trying it out may preferably serve to optimize a virtual facility with regard to a desired aspect. In this case, the step of assembling from the computer unit is particularly preferred, which may possibly suggest to the user improved and in particular optimal solutions for configuring the virtual equipment with regard to an aspect and in particular an optimum dynamic process. For example, the computer unit can suggest to the user an optimally cost-effective and/or space-saving and/or efficient solution for a configured piece of equipment. The computer unit can also make a suggestion with regard to optimum positioning of the virtual equipment elements in the virtual environment by identifying areas on which a virtual equipment element can be positioned. To this end, a particular embodiment may allow the user to determine one or more priorities according to which the optimization is to be directed.

In accordance with one aspect, the method further comprises the steps of:
- allowing an offer request for at least one virtual equipment element based on the parameter dataset;
- establishing an offer based on the offer request;
- allowing a goods order request;
- processing a goods order based on the goods order request.

This preferred embodiment enables the user, especially after testing and/or trying out the virtually configured equipment, to make an offer request and receive a corresponding offer for the respective physical equipment elements. The user can then make a goods order for the desired physical equipment elements. The advantage of this embodiment is, among other things, that the user can be familiar with the equipment prior to purchasing the physical equipment elements. In particular, the user and/or customer can store the virtual equipment on a server or another storage unit as a file. This has the advantage that a service representative of the supplier can access the virtual model of the physical equipment online from a distance, i.e. not on site, for example for the purpose of error diagnosis and/or technical consultation. The virtual model can thus serve as a so-called digital twin of the physical equipment. Given an overload of the physical equipment, in particular the wear of alternating elements of the physical equipment can be forecast and/or predicted. In addition, the user can receive from the distributor a message as to when an inspection or maintenance of the physical equipment should take place.

In accordance with one aspect, the method comprises a step of manual marking, preferably by finger on a touch screen or by mouse pointers, in the virtual environment with the aid of a screen, in particular for marking a virtual spatial point and/or a virtual and/or physical equipment element.

If a marking is to be carried out without physically applying a room and/or identity marker, the user can also set markers by hand in the virtual environment afterwards. For example, a function of the application may allow a finger to indicate in which direction the gravity is acting and/or at what location a virtual equipment element is to be placed and/or which physical equipment element is to be identified. The user can also mark a virtual connection in the virtual space, for example an outlet and/or a virtual connection of a virtual equipment element and/or a gas supply and/or an outflow. This allows the user to configure equipment with even less effort. In particular, a higher degree of flexibility can thereby be achieved. Particular preference is given to a function of the application that offers a step of providing possibilities. The application can thus provide the user with a possibility of setting an identity marking and/or a spatial marking manually in the virtual environment.

The invention also relates to a computer program product, in particular a computer program product stored on a computer-readable storage medium, for a computer-aided virtual configuration of a piece of equipment, in particular bioreactor equipment, wherein the computer program comprises computer-readable instructions which can carry out the following method steps during loading and execution on a suitable computing unit:
  determining a virtual environment based on a sensor dataset associated with a physical environment;
  determining a virtual arrangement at least one virtual and/or physical equipment element with respect to the virtual environment, wherein a parameter dataset is respectively associated with the virtual and/or physical equipment element; and
  predicting functionality and/or operating status of at least a portion of the equipment based on the parameter dataset and the sensor dataset.

A computer program product can be used in particular in the form of an application and/or app to cause the computer unit to perform the essential automated steps of the method for configuring the equipment in the augmented reality. By means of a user interface, the computer unit can execute the configuration together with the user's interactive inputs. Essential steps which require computing power are executed by the computer unit in order to support the user.

The invention further relates to an augmented reality (AR) system for virtually configuring a piece of equipment, in particular a bioreactor system, wherein the augmented reality system comprises:
  at least one sensor unit configured to detect a sensor dataset associated with a physical environment;
  a computer unit configured to perform the following steps:
    determining a virtual environment based on a sensor dataset associated with a physical environment;
    determining a virtual arrangement at least one virtual and/or physical equipment element with respect to the virtual environment, wherein a parameter dataset is respectively associated with the virtual and/or physical equipment element; and
    predicting functionality and/or operating status of at least a portion of the equipment based on the parameter dataset and the sensor dataset.

A system for generating an augmented reality, that is to say an augmented reality system in accordance with the invention, is embodied in a particularly simple manner so that advantageously an average user who has a smartphone and/or a tablet and/or a PC and a camera substantially needs no additional elements and only needs to download an application and/or software. Nevertheless, the augmented reality system can comprise special elements, such as a 3D-enabled camera or an infrared view device or an infrared camera. In particular, the normal or ordinary or average user and/or customer is enabled to configure a piece of equipment, in particular a system for processing biochemical and/or chemical media, in particular liquids, without any expenditure.

Physical environment and physical equipment element may also mean a physical or real environment and a physical or real equipment element. The term physical means in particular "real" or "objective".

In the following, particular and/or preferred embodiments will be described in detail with reference to the figures. Individual aspects, which in particular are not described in combination, can be combined with one another explicitly, provided that they do not mutually interfere.

The following are shown:

FIG. 1a is a flowchart of a chronological sequence of method steps for virtually configuring a piece of equipment in accordance with one embodiment;

FIG. 3 is a step of determining a virtual environment in accordance with one embodiment;

FIG. 4 is a step of determining a virtual environment in accordance with one embodiment;

Figure 10:
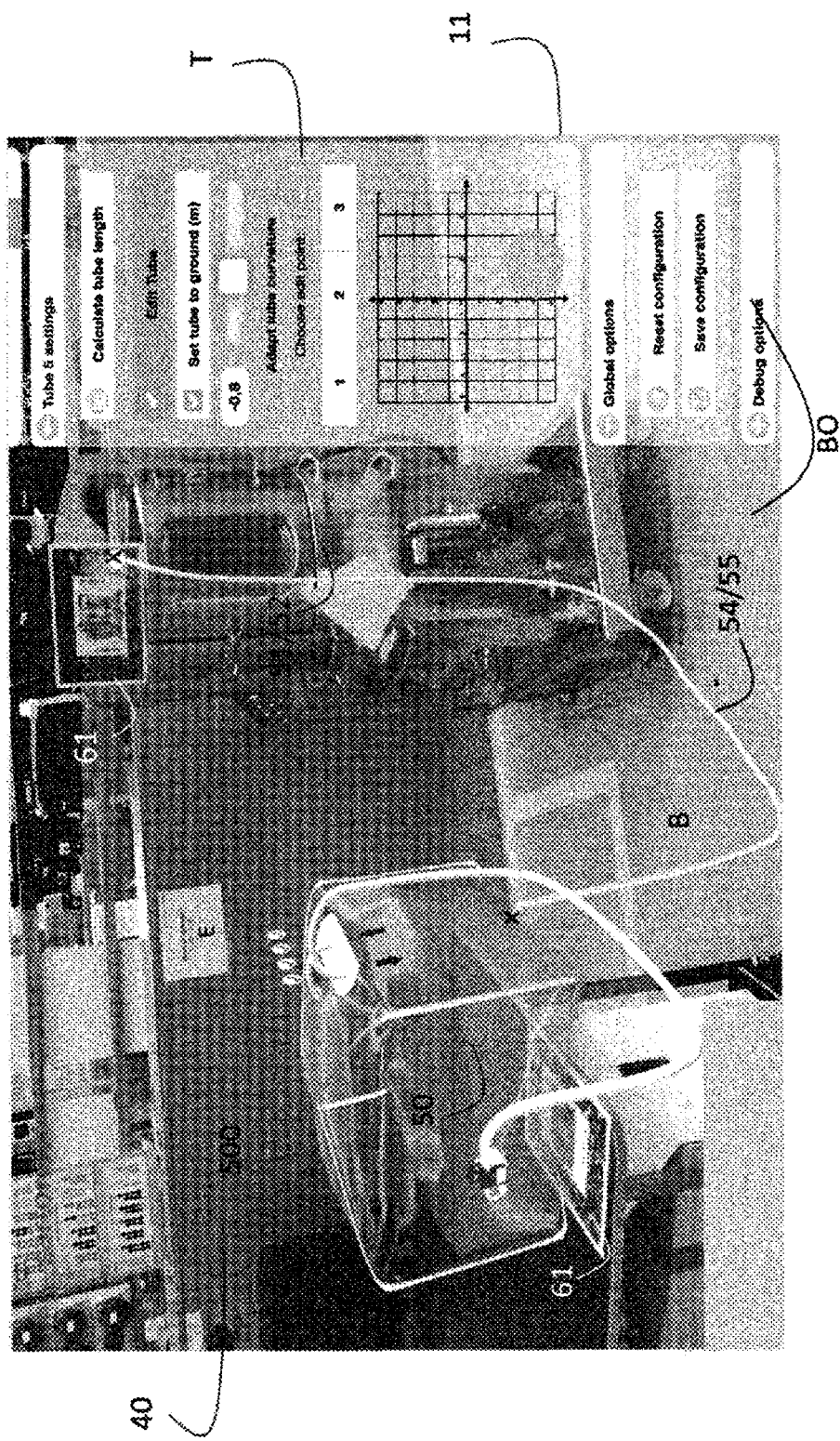
Figure 11:
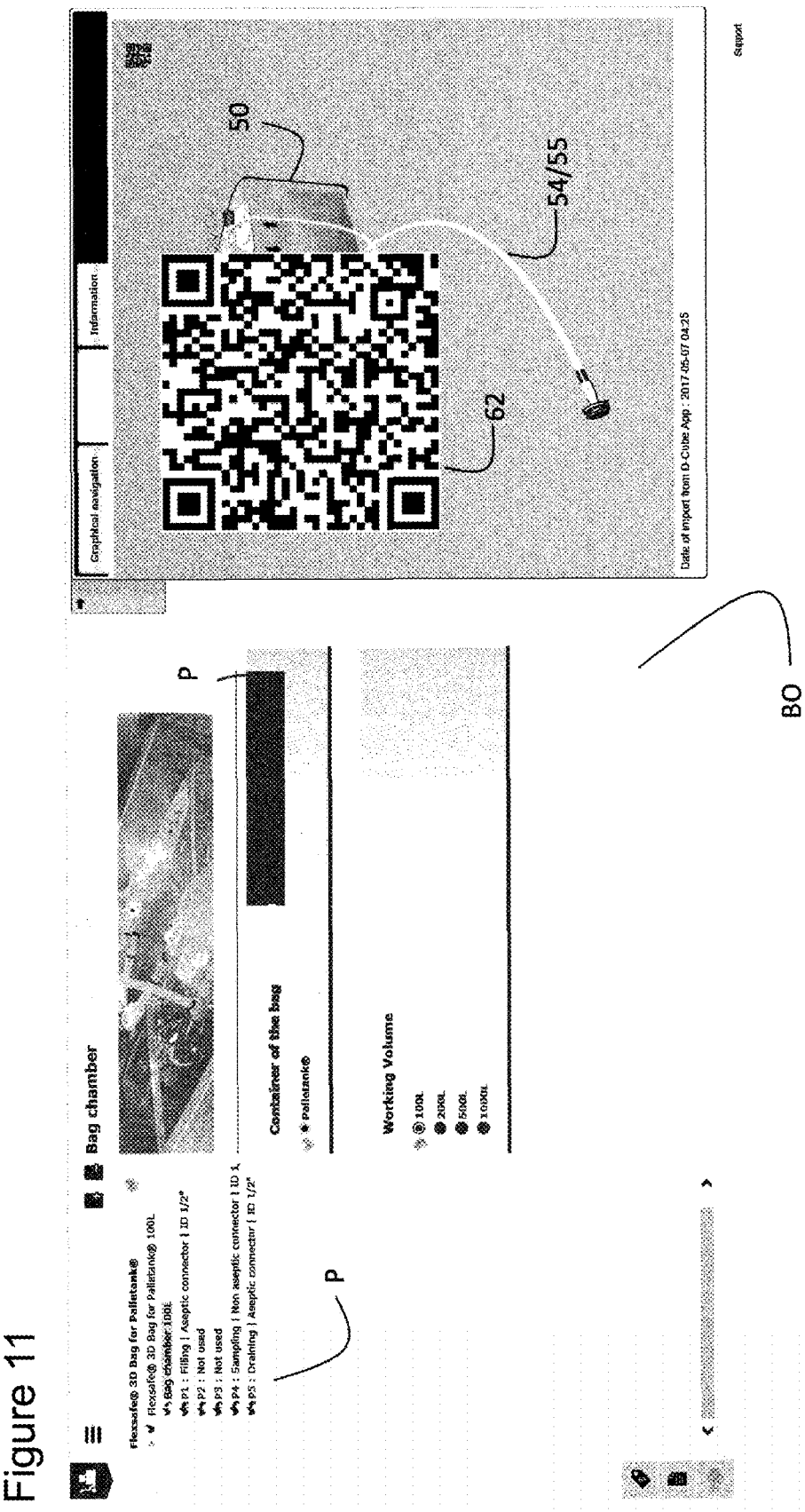
Figure 12:
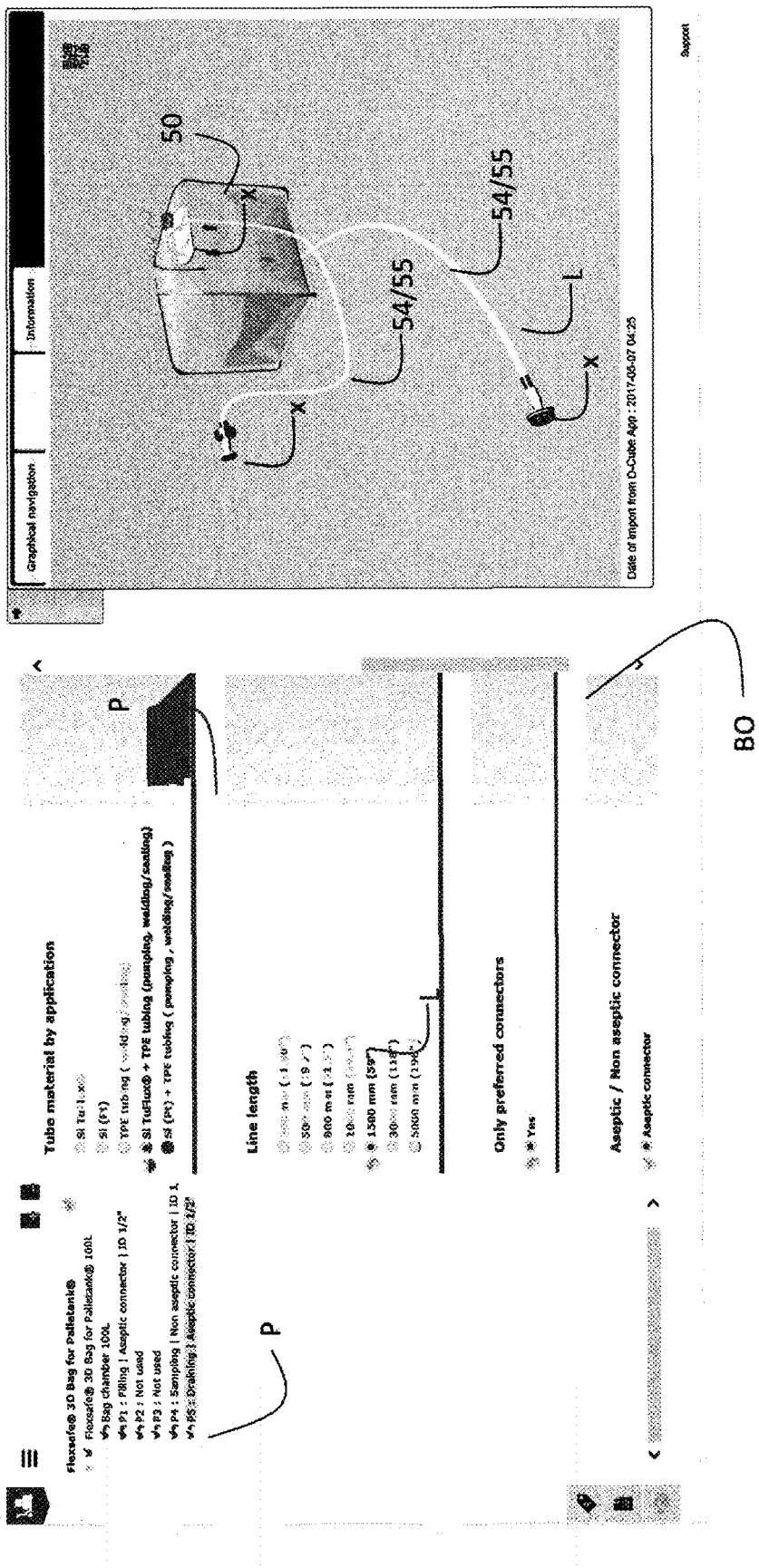
Figure 13:
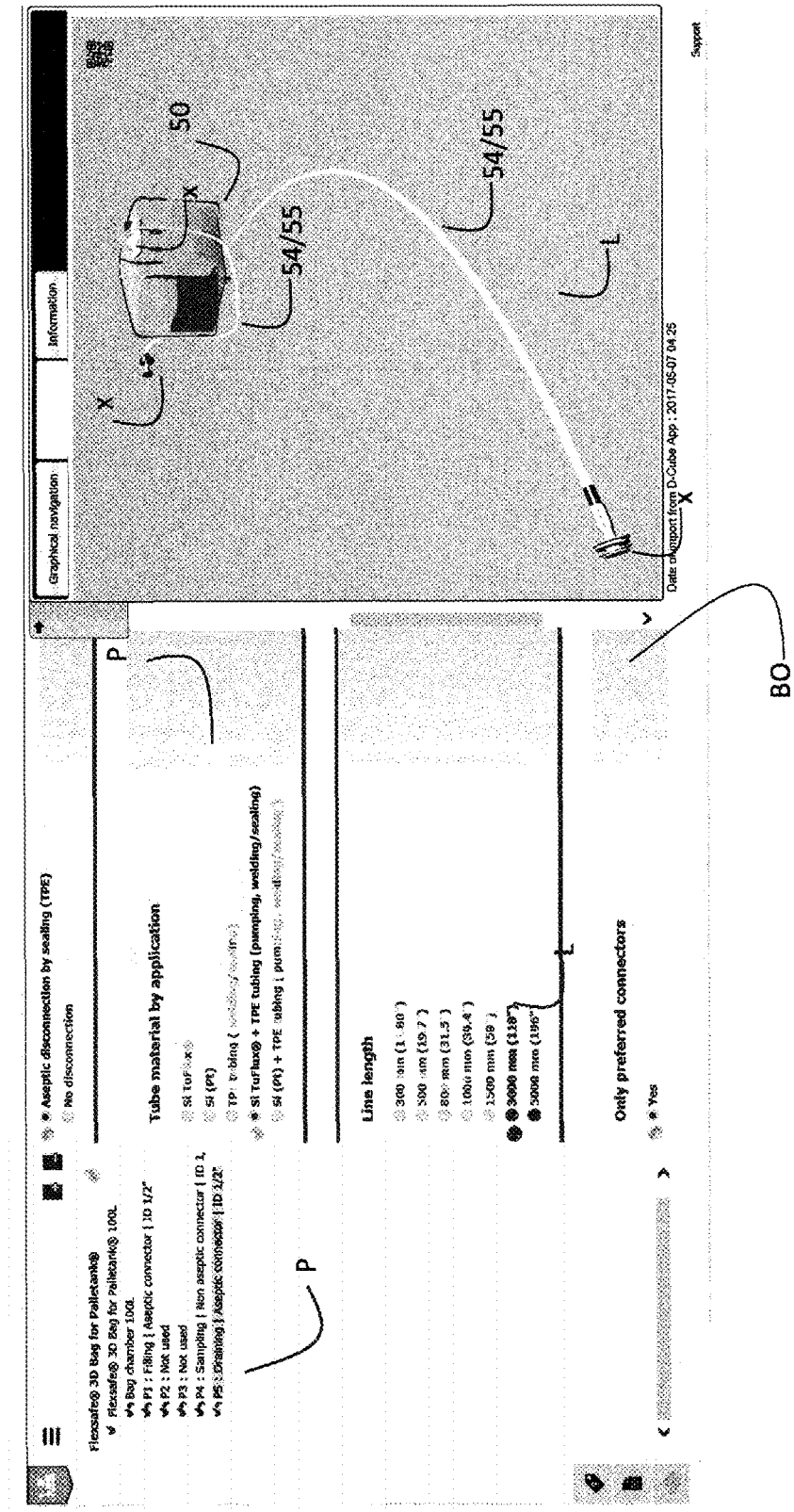

FIG. 10 a user interface in accordance with one embodiment;

FIG. 11 is a user interface in accordance with one embodiment;

FIG. 12 a user interface in accordance with one embodiment;

FIG. 13 a user interface in accordance one embodiment.

FIG. 1*a* is a flowchart of a substantially chronological sequence of method steps for virtually configuring equipment 500 in accordance with one embodiment. In particular, the method is carried out interactively between a computer unit 10 and a user 13. In other words, the user 13 enters inputs and the computer unit 10 executes necessary computing processes and/or communicates with the user 13 in this respect. In particular, a suitable application or a computer program product prompts the computer unit to carry out method steps. Below, it will be regularly mentioned that a computer unit 10 executes a method step. It is therefore substantially meant that an application prompts the computer unit 10 to carry out said method steps. Hereinafter, the method steps virtually configuring equipment 500 in accordance with one embodiment will be described in detail.

The method comprises a step of providing 100 of an augmented reality system or of an augmented (AR) system 1000, also referred to as an "augmented reality generation system". In particular, the augmented reality system 1000 provides a visual depiction of information which has a supplement from a representation (for example an image or video) with computer-generated additional information or virtual objects by means of fade-in and/or overlaying. The augmented reality system 1000 comprises a computer unit 10, at least one sensor unit 20 and in particular a screen 11 and preferably an application or a program or a computer program product. The augmented reality system 1000 may further comprise an identity marking 62, a spatial marking 33, and/or an object marking 61. The computer unit 10 may be a PC and/or a smartphone 12 and/or a tablet 12 and/or the like. A sensor unit 20 preferably comprises at least one camera, in particular a 3D-capable camera or camera system. A 3D-capable camera is or comprises in particular a unit for using a photogrammetry or a method which is designed for recording three-dimensional (3D-)coordinates or for 3D data acquisition. In particular, the 3D-capable camera is designed for 3D data acquisition and for spatial and/or object reconstruction. To this end, such a camera may comprise, for example, a laser scanner and a separate computer unit for digitizing the spatial coordinates. Any other technology for detecting three-dimensional or 3D coordinates is also conceivable. Additionally or alternatively, the sensor unit 20 may also comprise an infrared camera. Furthermore, the sensor unit 20 may also be designed to detect one or more environmental influences and/or interfering signals and/or interference. For example, the sensor unit 20 can detect noises, vibrations, temperatures and temperature fluctuations, electromagnetic fields and others, in particular over a course of time. To this end, a sensor unit may also comprise a clock or a chronometer. A screen 11 may be a computer screen and/or the screen of a smartphone 12 and/or a tablet 12, in particular with touch screen capability. An identity marking 62 may be used to identify an object. An identity marking 62 may in particular comprise a QR marking (in particular according to the ISO/IEC 18004:2006 standard). A spatial marking 33 can be used to determine spatial features or 3D coordinates and/or directions in space, for example a direction of the gravitational force. A spatial marking may likewise in particular comprise an AR marking and/or a QR marking (in particular according to the ISO/IEC 18004:2006 standard). However, an object marking 61 physically located in a physical environment 30 may define or determine or establish the destination of a virtual equipment element 50 in a virtual environment 40. In an augmented reality system designed to map or to determine a temporally changing virtual environment 40 in real time, an object marking 61 in the physical environment 30 may be moved and/or displaced, while the user 13 can monitor in real time how the virtual equipment element 50 would move virtually in the virtual environment 40. In this way, the user 13 can achieve, immediately or in real time, a virtual arrangement and positioning or "return" of the optimized virtual equipment element 50.

The method comprises a step of recording 110 a sensor dataset 200 of a physical environment 30 or a real environment such as a laboratory. In particular, the step of recording 110 a sensor dataset 200 may be performed or initiated by the user 13. To this end, the user 13 uses at least one function of the sensor unit 20 or of at least one sensor unit 20.

The sensor dataset 200 comprises digitized parameters of a real physical environment 30. The sensor dataset 200 particularly preferably comprises the spatial or 3D coordinates of at least parts of the physical environment 30. The digitization or the translation and/or transmission of the spatial features into data entries of the sensor dataset 200 can be effected on the one hand by means of the sensor unit, in particular the digital 3D-capable camera, directly or subsequently by means of the computer unit 10. Furthermore, a temperature and/or a temperature distribution in the space or in the physical environment 30 can be recorded statically or dynamically, for example by means of an infrared camera, in particular over a certain period of time. The data entries in the sensor dataset 200 may further comprise electrical fields, magnetic fields, electromagnetic fields, vibrations, light intensities, and/or other influences.

A physical environment 30 corresponds to a real existing space. Such space may comprise, for example, a laboratory and/or a hall and/or a similar environment. A sensor dataset 200 may preferably also comprise information about the direction of gravity 33 or the direction in which the weight force of a potential physical element or equipment element 51 would act. Such an indication can be made, for example, by means of the user 13 by positioning a physical marking 33 for indicating the direction of gravity, for example in the form of a printed arrow. Alternatively, the computer unit 10 can automatically recognize areas and/or recognize orientations in an image or an image by means of which the computer unit 10 can independently derive the direction 33 of the gravitational direction and in particular a weight force.

Moreover, the method comprises a step 120 of determining, in particular simulating a virtual environment 40 and/or mapping the physical environment 30 in the form of a virtual environment 40. The step of determining 120 comprises a step of reconstructing the captured physical environment 30 based on the recorded and digitized sensor data of the sensor dataset 200. In other words, a spatial or spatially temporal model of the physical environment 30 is exemplary reconstructed. This may also comprises, for example, an object reconstruction in which a three-dimensional object is reconstructed in the physical environment 30, for example a table or another piece of furniture, and substantially realistically mapped in the virtual environment 40.

Furthermore, determining 120 may also comprise generating field maps and/or overlaying sensor data, such as a spatial temperature distribution, with a 3D spatial depiction of the physical environment 30.

The method comprises a step of determining 130, 140 a virtual arrangement. This step 130,140 substantially comprises selecting 130 at least one virtual equipment element 50.

Method step 130 may, on the one hand, comprise a step 132 having the provision of selecting one or more virtual equipment elements 50. In particular, the computer unit can make a pre-selection of mutually compatible virtual equipment elements 50 and in particular suggest and present them to the user 13. This method step is followed by selecting at least one virtual equipment element 50. On the one hand, the user 13 or the computer unit 10 can make the selection. The computer unit can, for example, at least partially automatically select, based on predetermined criteria, which virtual equipment element 50 optimally satisfies the requirements of the user 13.

Additionally or alternatively, method step 130 may also comprise another step 132. Step 132 comprises providing a physical equipment element 51 that is already present and/or has already been installed and/or procured by the user 13 in the past. The physical equipment element 51 is or has in particular been offered and/or registered by the supplier, for example there can be data entries of a parameter dataset for the physical equipment element 51 in a database (e.g. a catalog or a product list). In its physical appearance, the physical equipment element 51 is preferably comprised by the sensor data set 200. In other words, the physical equipment element 51 may in particular be visible or faded in on an image, preferably a 3D image, which corresponds to an image of the physical environment 30. Step 132 further comprising identification of the registered physical equipment element 51 with a product entry in, for example, a catalog and/or a product list. This product corresponds to a virtual equipment element 50, that is to say a model of a physical equipment element which is or was offered for sale by the supplier. Identification can be done on the one hand by detecting a marked or characteristic shape characteristic or a shape feature by means of the computer unit 10. One or more structures or shape features of the physical equipment element 51 are compared with those of the virtual equipment element(s) 50. Alternatively, identification can be done by identifying an identity marking 62 attached to the physical equipment element 51 by the user 13 from the computer unit and assigning or allocating it to a virtual equipment element 50. In particular, the supplier may provide such an identity marking 62 for the products offered on his or her website for printing.

Step 132 also comprises the assignment of the registered physical equipment element 51 to a corresponding virtual equipment element 50 and to the parameter dataset by which the virtual equipment element 50 and thus also the physical equipment element 51 is characterized. This assignment substantially corresponds to the selection of a virtual equipment element 50, which is preferably carried out automatically by the computer unit 10. Additionally or alternatively, it is also possible that the user 13 e.g. carries out an assignment of the physical equipment element 51 to a virtual equipment element 50 manually or on the basis of a corresponding proposal list (e.g. in the form of a pull-down menu), in particular if the computer unit 10 does not identify the physical equipment element 51 or only incorrectly or not sufficiently or completely. If the computer unit 10 does not sufficiently or completely identify the physical equipment element 51, the list of suggestions can be narrowed down or customized taking into account the information partially recognized by the computer unit 10.

Figure 1B:
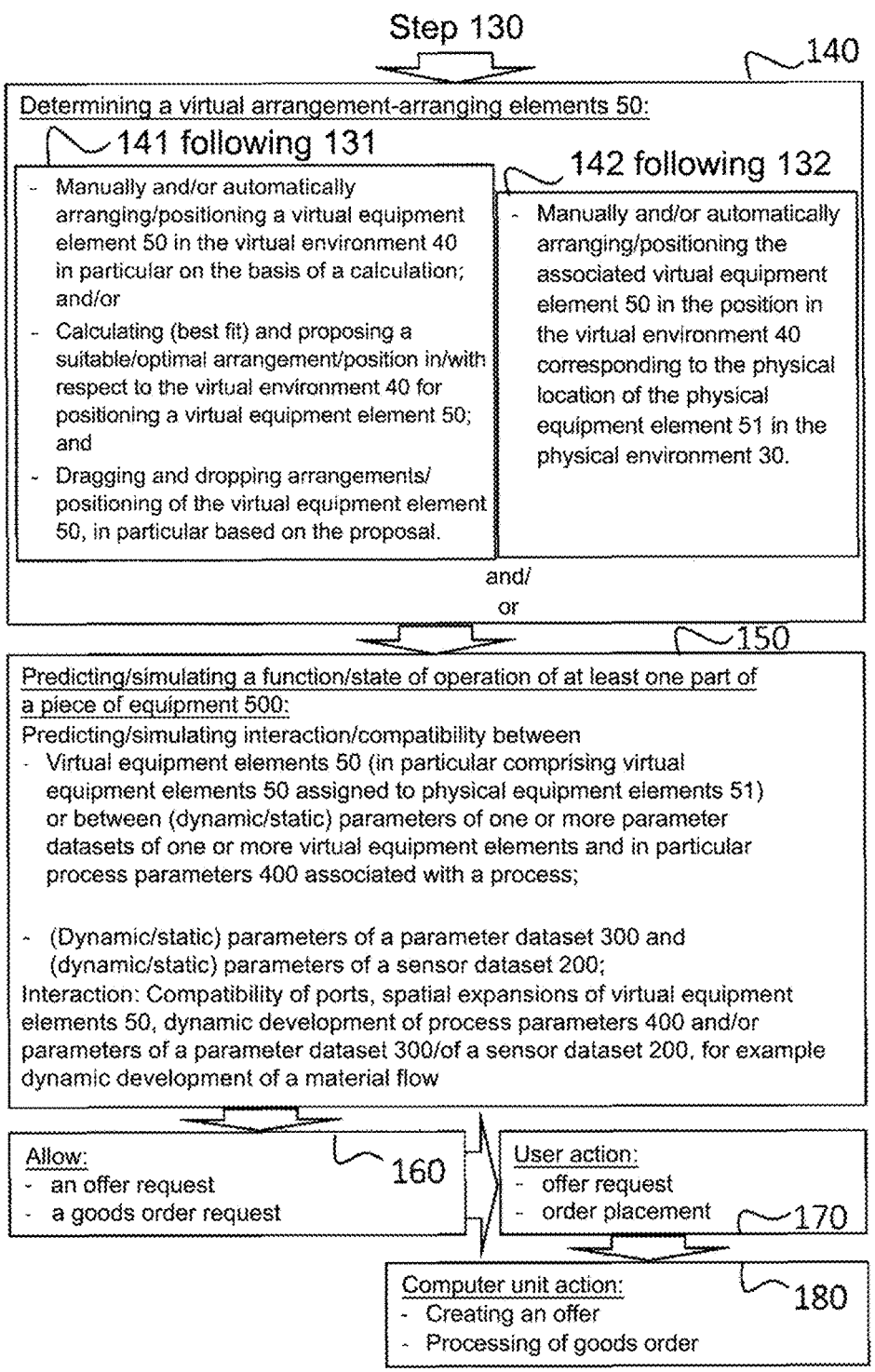
FIG. 1b is a flowchart of a chronological sequence of method steps relating to the method steps shown in FIG. 1a for virtually configuring a piece of equipment 500 in accordance with an aspect.

FIG. 1b is a flowchart of a chronological sequence of method steps 140-180 following method steps 100-130 depicted in FIG. 1a for virtually configuring equipment 500 in accordance with one embodiment. The determination of a virtual arrangement, which has already been described in part with reference to FIG. 1a further comprises a step of virtually arranging 140 or positioning at least one virtual equipment element 50 which was selected or determined in the previous step 130. Step 131, which involves selecting a virtual equipment element 50, e.g. from a pre-selected list, is followed by a step of manual and/or preferably automated virtual arrangement 141 or positioning of the selected virtual equipment element 50 with respect to (especially within) the virtual environment 40. In particular, a user 13 can position and/or displace the selected virtual device element 50 by "dragging and dropping" within the virtual environment 40. In this case, it is particularly preferred that the computer unit 10 recognizes or determines a suitable position for positioning the virtual device element 50 and suggests or displays the same to the user 13 so that the user 13 can position the virtual device element 50 at the proposed virtual location of the virtual environment 40 or confirm the positioning. Alternatively or additionally, the computer unit 10 may independently and automatically position the selected virtual device element 50 within the virtual environment 40. In particular, the computer unit 10 may independently and automatically perform a calculation by means of which an optimal virtual position can be determined. For example, the computer unit 10 may recognize that there is a virtual location in the virtual environment 40 that is free and/or which is, for example, sufficiently close to a port (e.g., an outlet) and/or other virtual equipment element 50. After determining a suitable and/or optimal virtual position, the computer unit 10 may automatically position the virtual equipment element 50 at the determined location in the virtual environment 40.

Virtual arranging 140 or positioning of at least one virtual equipment element 50 selected or determined in the previous step 130 may additionally or alternatively also comprise step 142 following the step 132 in which a virtual equipment element 50 has been selected or determined. Step 142 comprises automatically locating or positioning the virtual equipment element 50 at the virtual position in the virtual environment 40 corresponding to the physical location of the physical environment 30 on which the physical equipment element 51 is located. This step 142 can, for example, merely consist of assigning or allocating a corresponding parameter dataset of a corresponding virtual equipment element 50 to the identified physical equipment element 51. However, step 142 may also be similar to step 141 and correspond to automatically positioning the assigned virtual equipment element 50 in the virtual environment 40 at said predetermined virtual location.

The step of determining 130, 140 of a virtual arrangement of virtual equipment elements 50 of virtual equipment 500 may comprise, in particular, the step of selecting at least one virtual equipment element 50 (in particular a connection element) and positioning or switching it virtually between two virtual equipment elements 50. These steps comprise, in particular, the functional virtual connection of two virtual equipment elements 50 such that a connection can be established, for example, by means of a virtual tube and/or a virtual cable. To this end, the computer unit 10 can recognize which connections, in particular flow and/or tube connections and/or electrical and/or data transmission connections, are present at a virtual equipment element 50 or in the physical and virtual environment 30, 40. The computer unit 10 can preferably recognize which connection elements are particularly suitable with regard to the user's specifications and/or the virtual equipment elements 50 and/or the virtual environment 40 and are in particular compatible with possible virtual connections of the virtual equipment elements 50. The computer unit 10 may further make a calculation which determines how long a connection element should optimally be. To this end, the computer unit 10 for calculating the optimal length L may involve the determined gravitational direction and a corresponding gravitational force when the sensor dataset 200 contains this information. The user 13 may additionally or alternatively determine the length L of a selected virtual connection element and/or vary if necessary, as will be described below by way of example with reference to FIG. 7 and/or FIG. 10-12.

The step of determining the virtual arrangement 140 is followed by a step of predicting 150, in particular a simulation, in such a way that an operating status of virtual components or elements, in particular virtual equipment elements 50 of the device 500 is estimated and/or predicted and/or simulated in advance. An interaction between virtual components or elements, in particular virtual equipment elements 50, can also be predicted and/or simulated. An operating status also be characterized by means of a marking. For example, a marking may indicate that a physical equipment element 51 is out of operation. In this case, this physical equipment element 51 can be neglected substantially in terms of its functions when digitizing or translating into a virtual model.

In this step 150 static and/or dynamic, i.e. time-dependent parameters can be predicted and/or simulated. Compatibility between two virtual components/elements, in particular virtual equipment elements 50, can preferably be checked or tested. The calculation of such static and/or dynamic parameters may be based on the static and/or dynamic or data entries of sensor dataset 200 and/or parameter dataset 300.

In terms of checking compatibility(s), it can be checked whether a virtual equipment element 50 can be connected to a virtual power plug corresponding to a real physical power plug in the physical environment 30. In particular, it is of interest here as to whether the power supply is compatible with the virtual equipment element 50. In another possible case, it is possible to check whether a gas and/or liquid supply and/or discharge is suitable to be connected to the virtual equipment element 50, for example, whether the requirements and conditions with regard to the conditions, such as pressure and/or current, are compatible. In yet another case, it can be checked whether two virtual equipment elements 50 are compatible with one another or can at least be harmonized or matched to one another (for example by means of suitable intermediately switching components) so that these can be connected to one another. For example, it can be checked whether the operating ranges of two virtual equipment elements 50 do not overlap with one another with regard to a condition or a parameter, if this should be necessary. This may be the case if a virtual equipment element 50 can be operated within a determined operating range that does not at least partially overlap the operation pressure range of another virtual equipment element 50, wherein an open connection is between both virtual equipment elements 50. By way of further example, a virtual equipment element 50 may be connected to a virtual outlet having a false voltage value and/or an insufficient current value. Checking compatibility may also concern only the compatibility of ports and/or the spatial extent with respect to possible positioning in virtual environment 40 of virtual equipment elements 50. In other words, it can be checked, for example, whether a virtual equipment element 50 in the virtual environment 40 has sufficient space for positioning.

The step of predicting 150 an operating status may further comprise the step of simulating a dynamic process parameter 400 and/or a flow of material between two virtual equipment elements 50. Process parameters 400 can be determined beforehand by a user and/or from a database and transmitted to the computer unit 10. For example, a user 13 may determine that he or she wishes to run a particular biochemical reaction within a virtual equipment element 50. To this end, the user 13 can determine or establish the type of process or specific reaction which is desired, the quantity of the desired educt and/or product, the temperature and/or its time profile, and the like as respective process parameters 400 (for example to be input into a table or into a dataset). On the basis of the computer unit 10 for available data, in particular, among other things, the process parameter 400, the sensor dataset 200 and the parameter dataset 300, a simulation of a biochemical and/or chemical and/or thermodynamic and/or biological process can be carried out. To this end, known relationships, for example dependencies of various parameters, are used for simulation. Depending on the number of parameters to be included, a simulation can be arbitrarily complex or just a very rough approximation. The virtual environment together with the simulation corresponds to an arbitrarily complex model of reality that would occur under the predetermined circumstances characterized by the given parameter entries. In particular, the prediction may take into account any influences corresponding to one or more entries in a sensor dataset 200 in the simulation. For example, a real light source 34 as shown in FIG. 2*a* and/or a temperature fluctuation may have an effect on a process that may be predicted by means of the simulation. This would be the case, for example, if a light source, for example a window through which daylight passes, would influence the process of photosynthesis of a biological medium. A typical temperature fluctuation in the physical environment 30, for example between day and night times and/or between winter and summer times, which was measured or recorded in particular beforehand by means of the sensor unit 20, may also have an effect on the process or the reaction. Such influences and their effects, which are of interest to the user 13, can be at least approximately predicted or estimated by the simulation. The aim here is substantially to track the goal of achieving an optimal configuration of the device 500 in advance. For example, in case of detecting interfering light sources and/or temperature variations and corresponding unsatisfactory simulated process results, the computer unit 10 may suggest other products that can suppress these predicted effects. Such products or physical elements of furniture may comprise, for example: a darkening element, as a curtain or screen, which allows light from disturbing light sources to be intercepted, and/or a thermostat to actively compensate for external temperature variations. Such products can also already be integrated or integrated into a physical device element 51 and supplied as special equipment.

The step of predicting 150, in particular simulating, can be followed by the transmission of a status message to the user 13 and/or to the screen 11, in particular to the user interface, whether the equipment 500 can be operated substantially error-free and properly, and in particular whether a process achieves a desired success. An error message, on the other hand, would indicate that basic problems are predicted or follow the simulation. The result of the simulation may also already identify problems in advance and indicate that special equipment and/or alternative physical equipment elements 51 are needed to properly operate the device 500. In particular, a user 13 may already try out or test a virtual model of a self-configured device 500 in advance and/or be familiar with the functions.

Following the transmission of a status message, the user 13 may decide whether to purchase one or more physical equipment elements 51 corresponding to virtual equipment elements 50 of the configured device 500. To this end, the method allows, in one step 160, the user 13 to send an offer request and possibly a goods order request to one or more suppliers. In another step 170, the user 13 makes the corresponding actions, namely the offer request and the order task. This step may comprise, for example, the input of personal data of the user 13. In step 180, the offer request is processed, whereupon an offer is created. Furthermore, the order task is processed according to the offer and in particular the personal data of the user 13 and possibly forwarded and processed to the distributor or seller or the sales unit.

In particular, the method according to FIGS. 1*a* and 1*b* can be used for individual consultation by a representative or seller and/or service personnel. The model of the configured device 500 can also be stored in a data memory. If required, a service representative can access the model (e.g. online), especially for error analysis, and diagnose possible weak points or errors. If the user 13 keeps a logbook, in particular a digital logbook, of the operation of the physically acquired equipment or installation, this record of the logbook can be loaded into an application that simulates the operation of the equipment 500 based on the stored model and can, for example, draw attention to possible wear. Furthermore, an automated message can be sent to the user 13 when maintenance and/or repair and/or inspection of the equipment 500 is required. In this case the model is substantially also used as a so-called "digital twin".

FIG. 2*a* illustrates a method step in accordance with an embodiment which is executed in step 110 in FIG. 1*a* and in particular corresponds substantially to step 110 in FIG. 1*a*. The method step 110 can be executed by means of an Augmented Reality system 1000. An exemplary augmented reality system 1000 comprises a smartphone 12. In this step 110, the user 13 takes a photograph 31 or image of a physical environment 30, in particular a photogrammetry of a physical environment 30 by means of a detector (e.g. by means of a camera 21 of a smartphone 12). This step can alternatively also be automated and executed by a computer unit 10. The map 31 of the physical environment 30 can be seen on the display screen 11 of the smartphone 12. The smartphone 12 comprises or is connected to a computer unit 10 and a screen or display 11 in particular a touch screen (or touch screen) and a sensor unit 20 which comprises the camera 21. The execution of the computing steps, in particular of the simple, less complex computing steps, can be carried out in part by means of the computer unit 10. Complicated Computing steps which require a high computing power can be carried out at least in part by means of an external computer unit or a cluster to which the smartphone 12 can be connected. Results of these computing steps are then transmitted only to the smartphone 12. A corresponding application (or organizer) can be loaded onto the smartphone 12 and executed in conjunction with or during the method. The application together, by means of an appropriate user interface, may in particular be designed to guide or direct or lead the user 13 through the configuration of equipment and/or to prompt the user to enter one or more inputs.

In the physical environment 30, a marking for indicating a gravitational direction 33 is positioned, which is also imaged in the image 31 of the physical environment 30. This marking can only consist of an arrow which implies the direction of gravity. Alternatively or additionally, the gravitational direction can be determined by means of a sensor of the smartphone 12. In the physical environment 30, a physical equipment element 51 is further positioned. The physical equipment element 51 is a bioprocessing system which is already registered in a product database and can be recognized and identified by the computer unit 10. If the physical device element 51 corresponds to a component that is not registered, then the spatial structure can be detected and digitized or translated into a three-dimensional virtual model.

Figure 2B:
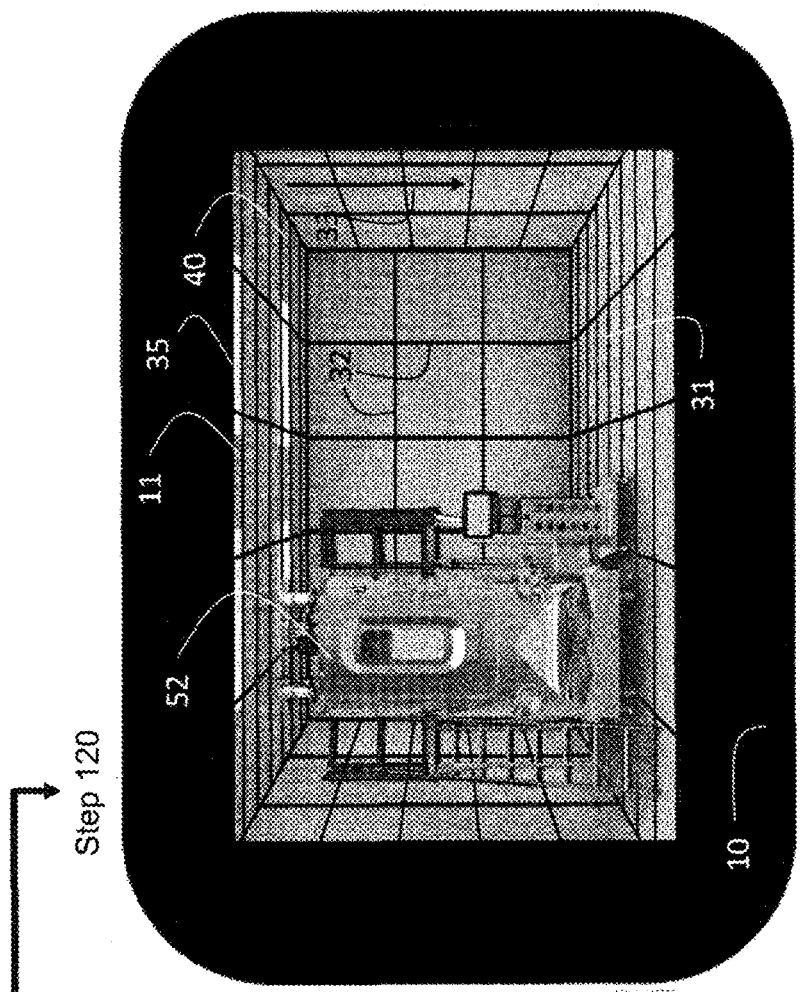
FIG. 2b is a step of digitizing the sensor data in accordance with one embodiment.
Figure 2A:
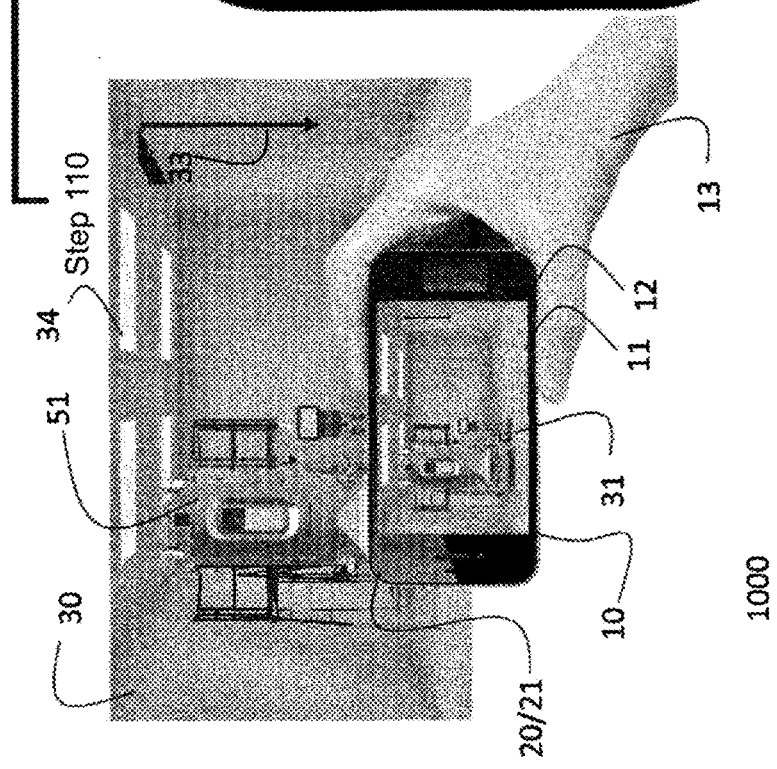
FIG. 2a is a step of receiving sensor data by the user in accordance with one embodiment.

FIG. 2*b* illustrates a method step in accordance with an embodiment, which is carried out within the framework of step 120 in FIG. 1*a* and in particular substantially corresponds to step 120 in FIG. 1*a*. This step can also be included, at least in part, in step 110. In other words, two steps 110 and 120 are described separately, which may nevertheless run in one step or at least partly at the same time and/or may be substantially linked.

FIG. 2*b* shows a smartphone or tablet 12 with a screen or display 11 showing FIG. 31 of the physical environment 30 in accordance with an embodiment. The smartphone or tablet 12 is not necessarily the device with which the sensor data 200 was recorded. It can also be, for example, a computer or personal computer (PC) onto which the sensor data 200 are loaded or transferred. The map 31 of the physical environment 30 is substantially a component of the sensor dataset 200.

It may be preferred that in step 120 the sensor dataset 400 is processed along with the map 31 of the physical environment 30 such that a virtual environment 40 is generated. In addition, the virtual environment 40 can also be generated or generated shortly after the recording of the sensor dataset 200, that is to say in step 110, by means of a computer unit which is integrated in a digital camera. Alternatively, the map 31 of the physical environment 30 may already substantially correspond to a virtual environment 40. In addition, spatial information, for example the 3D coordinates of a surface of the physical environment 30, may also be indicated by a spatial marking arranged on the surface of the physical environment 30. This information about the room can only be digitized by evaluating the position of the spatial marking. Similarly, an object marking 61 (or more) may be placed on or on a surface of the physical environment 30. The physical area in the physical environment can be translated into a virtual area in the virtual environment 40 on the one hand. At any rate, the virtual equipment element 50 corresponding to the object marking 61 is positioned and/or aligned and/or displayed at the virtual location defined by the object marking 61 relative to the virtual environment 40.

In this regard, it should also be mentioned that the method in accordance with the invention generally does not necessarily require that a physical environment 30 be imaged on a screen 11. In other words, the method cannot alternatively be subject to the "what-you-see-is-what-you-get principle". In this case, the method can also be quite abstract, for example by means of a text editor in which the user can enter and/or edit a source code on the basis of which the method steps can be processed and/or executed.

The light source 34 shown in FIG. 2*a* can be recognized or reconstructed in the virtual environment of FIG. 2*b* as a functional element, namely as a virtual light source 35.

FIG. 2b not only shows FIG. 31 of the physical environment 30 on the screen or display 11, but a virtual environment 40 serving as a digital model of the physical environment 30. The depicted grid 32 indicates that the three-dimensional properties of the physical environment 30, that is to say the 3D coordinates, have been digitized.

Preferably, the spatial structure of a physical equipment element 51 can be mapped in the virtual environment 40. In particular, the physical equipment element 51 is a known or registered element. Spatial structures of one or more other unregistered physical equipment elements 51 or components, such as tables, laboratory benches, outlets and/or gas supplies or similar, can also be mapped in the virtual environment 40. These are visible in step 120 as 3D reconstructed objects or images 52 of physical equipment elements 51 in the virtual environment. In step 120, FIG. 52 of a registered physical equipment element 51 is initially unidentified, i.e. the computer unit has not yet recognized what the physical equipment element 51 is and no assignment has been made to a virtual equipment element 50.

FIG. 3 shows the process steps 130 to 140, in particular steps 132 to 142 in accordance with one embodiment, in more detail at least in part. In this step, the computer unit 10 recognizes that the image 52 of the physical equipment element 51 is a known, in particular registered, image. In this case, the physical equipment element 51 may be aligned with products of a product catalog or a product list. For example, a product may be digitally presented in a database as a virtual equipment element 50. At least, however, the product may be associated with a parameter dataset. For example, the parameter dataset of the corresponding product may also comprise 3D coordinates of the spatial structure of the product. These 3D coordinates of the spatial structure of the product can then be aligned with the 3D coordinates of the mapping of the physical equipment element 51. If there are one or more matches in the structural features between the physical equipment element 51 and the product, the computer unit can recognize the physical equipment element 51 on the basis of the image 52 and assign it to a product, in particular a virtual equipment element 50, but at least to a parameter dataset 300. This step corresponds to the automatic identification of a physical equipment element 51.

Said step of identifying 120 may be carried out under assistance by a user 13, e.g. if the computer unit 10 failed to perform the identification and/or should not automatically search for a registered physical equipment element 51 to be identified, because this would require, for example, too high a computing power. This is exemplified in FIG. 3. In that case, the user 13 can indicate, by indicator 60 (e.g. mouse pointer 60 and/or by means of touch on the touch screen), where a possible physical equipment element 51 to be identified is imaged in the virtual environment 40. On the one hand, by displaying the user 13, the arithmetic unit 10 can be caused to start a search run itself, which in particular results in a physical device element 51 being automatically identified. On the other hand, the computer unit 10 may display a selection of possible products, in particular virtual equipment elements 50 to the user 13, wherein the virtual equipment elements 50 have similar structural spatial features to those of the physical equipment element 51. For example, it can be various generations and/or series of construction and/or series of a product which appears to be similar or appears to be the same. In this case, the user 13 can determine the appropriate virtual equipment element 50 from the proposed selection (e.g. as a list with one or more icons or depictions and/or as a drop-down menu) by clicking or selecting it and/or clicking a "select button" as indicated in FIG. 3.

By assigning the physical equipment element to a virtual equipment element 50 or after this association, an arrangement 140 is made, in particular an automatic arrangement 142 of the virtual equipment element 50 at the virtual position of the image 52 of the physical equipment element 51. On the other hand, a virtual equipment element 50 corresponding to the physical equipment element 51 may also be overlaid and/or replaced in the virtual environment of the image 52 of the physical equipment element 51. It is possible to preferably displace and/or rotate and/or position the virtual equipment element 50 corresponding to the physical equipment element 51 and/or the image 52 of the physical equipment element 51 in the virtual environment.

In FIG. 4 method step 130, in particular step 131, is illustrated in more detail in accordance with one embodiment. On the user interface, which is displayed on screen 11, the computer unit 10 offers a list 57 of one or more virtual equipment elements 50, from which the user 13 can select or determine a virtual equipment element 50. In particular, the computer unit 10 makes a pre-selection of virtual equipment elements 50 with respect to an aspect, which can be predetermined by the user 13. For example, a list 57 of virtual equipment elements 50, which are indicated by way of example by "product 1", "product 2" and "product 3" can be displayed, wherein these are compatible with one another and/or assigned to the already identified physical equipment element 51 or virtual equipment element 50.

The user 13 can select a corresponding virtual equipment element 50 from the list 57 with the indicator (e.g. mouse pointer) 60 by clicking on the displayed article or a corresponding "select button". Alternatively, the computer unit 10 may also select a corresponding virtual equipment element 50 from the list 57, particularly if it is a virtual equipment element 50 that is necessary in the equipment 500 for proper functioning. For example, a user 13 can select a virtual pump from a list 57 or a range or product catalog. The computer unit 10 can thereby be made to select a suitable oil for the physical pump corresponding to the virtual pump, so that the physical pump can be filled immediately with the oil and put into operation after purchase and delivery.

Figure 5:
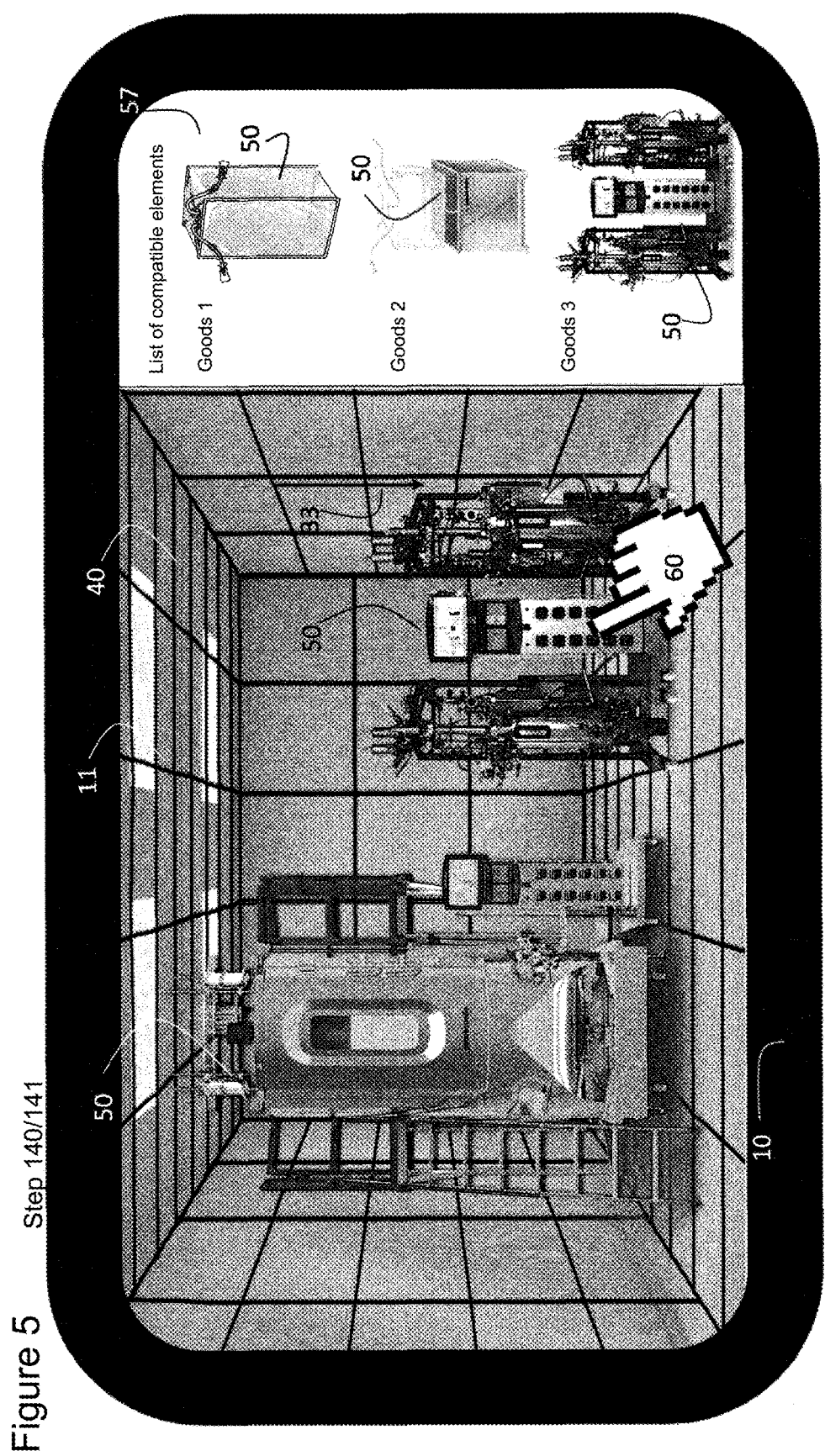
FIG. 5 is a step of determining a virtual environment in accordance with one embodiment.

FIG. 5 illustrates method step 140, in particular step 141 in more detail in accordance with one embodiment. The user 13 can, by means of the indicator (e.g. mouse pointer) 60, "drag and drop" the selected virtual equipment element 50 to a location within the virtual environment 40 or with respect to the virtual environment 40, in particular by taking into account the weight force or the gravitational direction 33. An input via the touch screen, for example by means of the finger, is also conceivable. The user 13 may displace and/or rotate and/or reposition the virtual equipment elements 50 in the virtual environment 40.

In particular, the computer unit 10 can calculate and/or propose and/or perform an optimal arrangement of the virtual equipment elements 50 with respect to a specific (predetermined or predeterminable) aspect. For example, an outlet already recognized by the computer unit in the virtual environment 40 can be taken into account when arranging a virtual equipment element 50. Or in another example, the computer unit 10 can recognize that a location or a virtual position in the virtual environment 40 may be rather unsuitable for a virtual equipment element 50 and/or a process, in particular if the sensor data set 200 indicates or allows conclusions to be drawn on interfering signals, for example interfering light sources 34 and/or interfering temperature fluctuations at this virtual location.

The computer unit 10 may also recognize that a virtual location is already "occupied" by a component, in particular a virtual equipment element 50, and/or that the virtual environment 40 does not provide enough space to locate a particular virtual equipment element 50. In this case, the computer unit 10 may propose another option and/or issue a corresponding error message.

Figure 6:
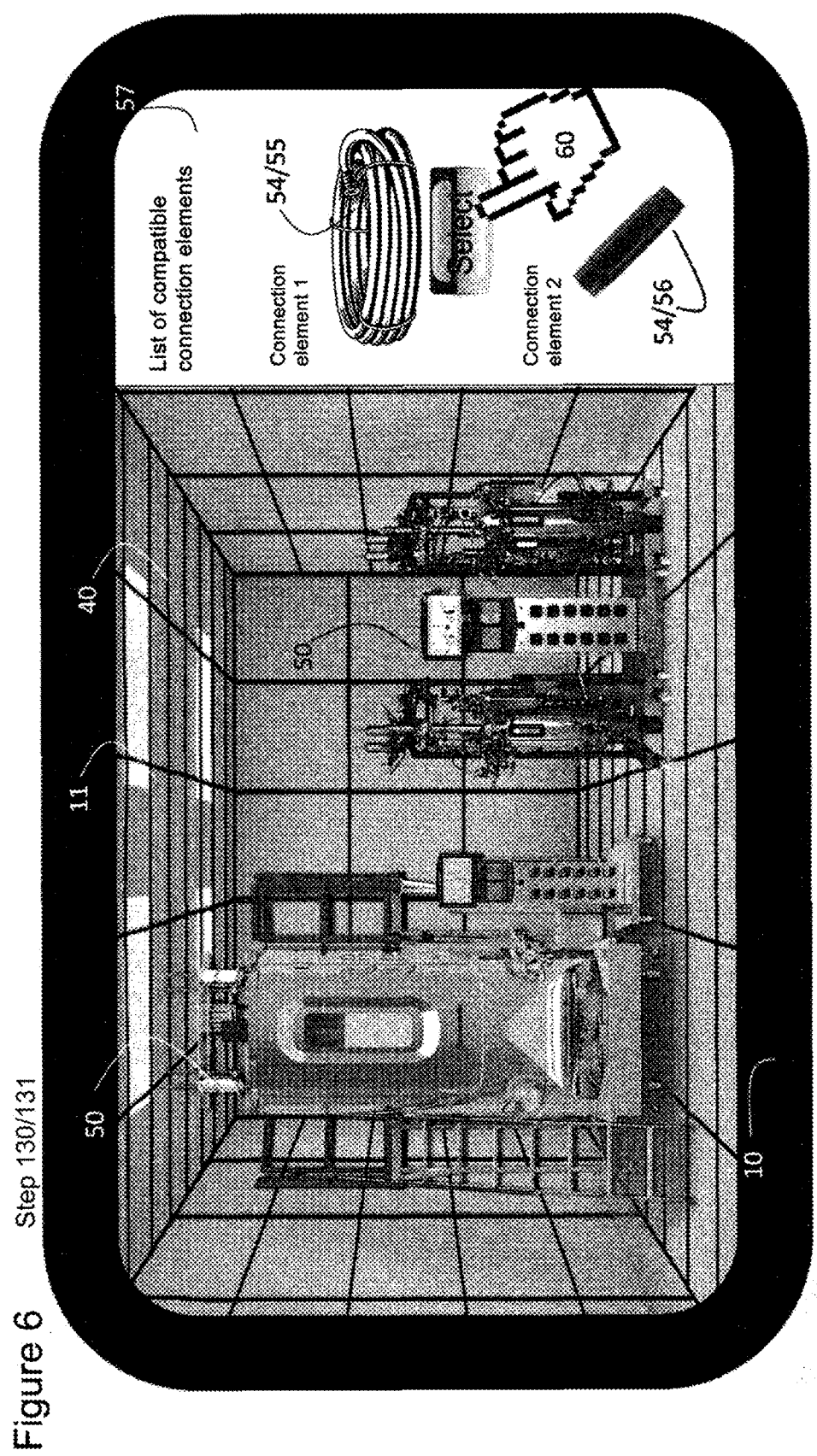
FIG. 6 is a step of determining a virtual environment in accordance with one embodiment.

FIG. 6 describes a particular method step 130 in more detail, in particular a step 131 in accordance with one embodiment, namely that of selecting 131 a virtual equipment element 50 corresponding to a virtual equipment element 54. A product pallet, in particular a list 57 of compatible virtual equipment elements 54, is imaged on the user interface or the screen 11. FIG. 6 shows a virtual tube 55 and a virtual adapter and/or connection piece 56. Similarly or identically, as shown in FIG. 4 the step of selecting 130 and 131 of a virtual equipment element 50, the user 13 and/or the computer unit 10 can select a virtual connection element 54 from the offered selection 57. In particular, it is also a pre-selection of virtual connection elements 54 which are compatible with a previously selected virtual equipment element 50.

Figure 7:
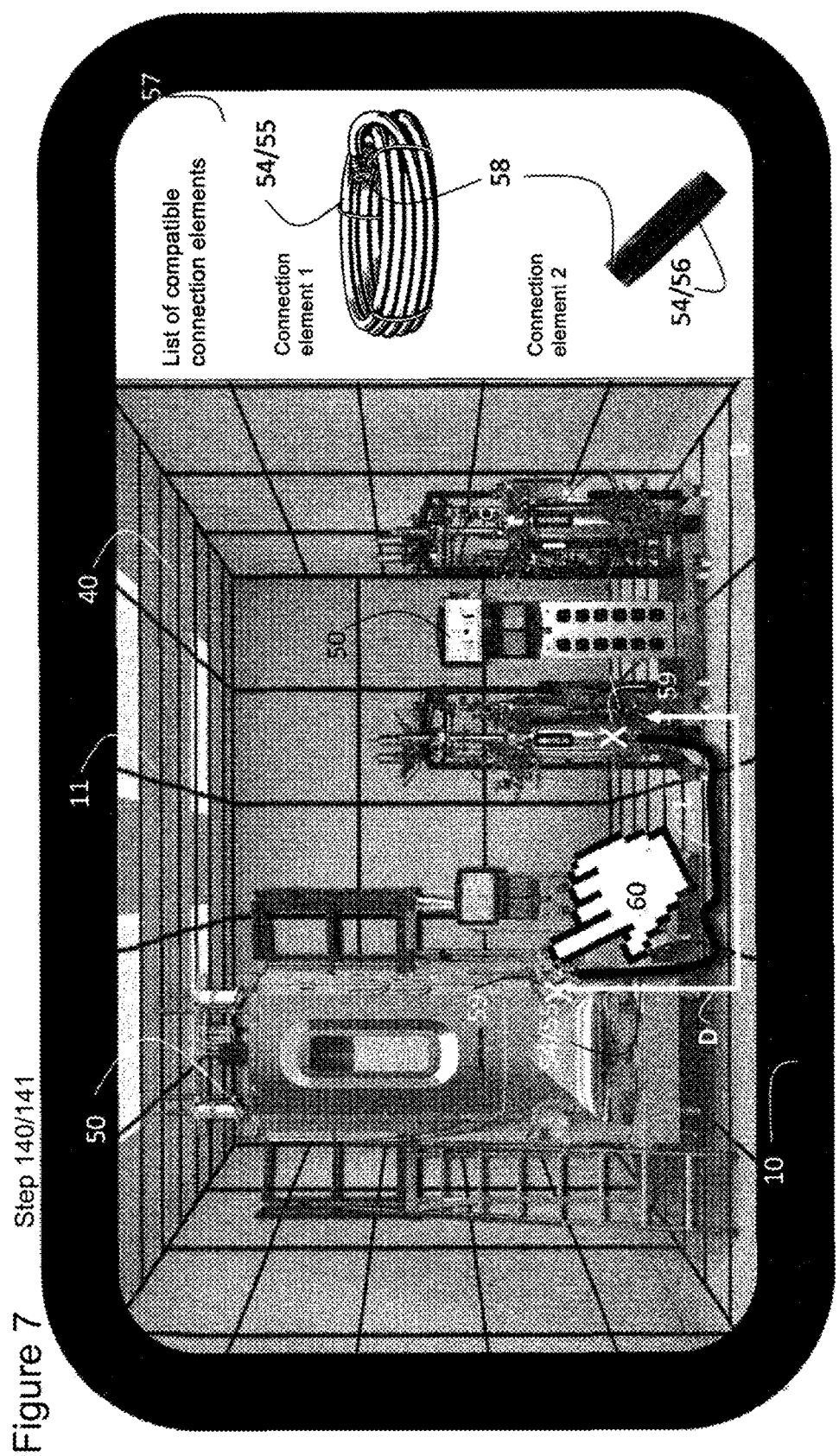
FIG. 7 is a step of determining a virtual environment in accordance with one embodiment.

FIG. 7 shows a particular method step 140 in more detail, in particular a special step 141, in accordance with one embodiment in which a virtual connection element 54 is arranged in the virtual environment 40. The method particularly preferably comprises a step of identifying a port or connector x (reference numeral 59) of a virtual equipment element 50 and/or a virtual or physical port x, for example an outlet or a water supply belonging to the infrastructure of the physical environment 30. In particular, the method can comprise a step of the automatic virtual connection of virtual ports x by means of the virtual connection elements 54 by the computer unit 10. The method can also preferably comprise a virtual connection of virtual ports x by the user 13. To this end, the computer unit 10 can assist or support the user 13 by marking virtual ports x for the user 13 in the virtual environment 40. The user 13 can virtually arrange the selected connection element 54 at the virtual ports x by clicking or "dragging and dropping" and thereby virtually connect the virtual equipment elements 50. It is also conceivable for the port x to have an AR marking for its recognition. Furthermore, the port x can also itself serve as a spatial marking.

The computer unit 10 can preferably determine in one method step, taking into account gravity or gravity direction 33, what distance D is between virtual ports and what length a virtual connection element 50 must have so that a virtual connection is achieved. In particular, it can be taken into account that the connection element 54, for example a hose 55 is "sagging" and/or is running at least partially along the virtual floor B. In particular, the user 13 can manipulate or change the length L of the virtual connection element 54. For example, the user 13 can enter a length L in a field of the user interface and/or dynamically change a length L by means of a slider. In a preferred method step, the computer unit 10 can also be caused to optimize a length L of the virtual connection element 54 with respect to an aspect.

In general, the step of determining a virtual environment 130, 140 may comprise steps 131, 141 and/or steps 132, 142. In other words, steps 131, 141 may be independent of steps 132, 142. However, determining a virtual environment 130, 140 preferably comprises steps 132,142 and this has the advantage that a new virtual equipment element 50 is virtually tested and possibly acquired by the user 13.

In particular according to steps 110 to 140 the virtual environment 40 also comprises functional features in addition to the spatial properties or features, provided that a special virtual function, for example concrete processing of a medium, is assigned to the virtual equipment element 50.

Figure 8:
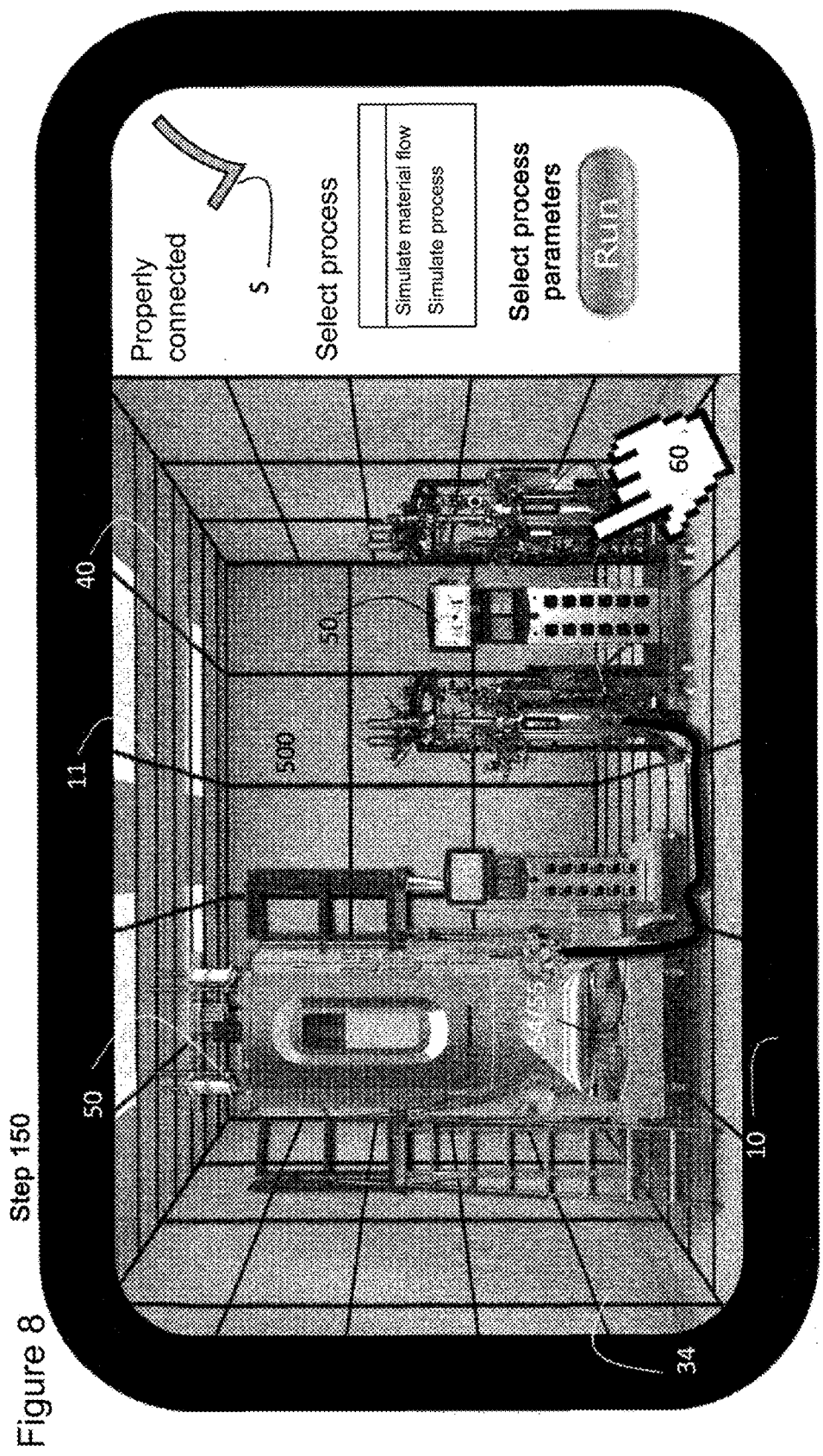
FIG. 8 is a step of determining a virtual environment in accordance with one embodiment.

FIG. 8 illustrates the method step of predicting 150 (in particular simulating) an operating status in accordance with one embodiment. In a method step, for example, it may be predicted whether the virtual connection 54, 55 is correct. This can mean that it is checked whether all relevant virtual ports x are compatible with one another, whether the connection elements 54, 55 have the required features, for example a suitable length L, and whether the correct virtual ports x have been selected. The correct virtual connection can be indicated or communicated to the user 13 by a corresponding status message S. An error message to that effect would indicate the faulty virtual connection. The computer unit 10 can also (in particular additionally) point out at least one problem in concrete terms and make 13 concrete proposed solutions to the user, for example a suitable virtual adapter 56 from the product range or a suitable length L of the connection element 54.

In particular, in the case where a simulation is to be performed, the user 13 can select an operation from possible operations in one step. For example, a material flow can be simulated or calculated on the basis of the connected virtual equipment elements 50 which have containers. To this end, the user 13 can also select and/or enter and/or change process parameters 400.

For example, the user 13 may indicate how unique the volume of the medium should be and in what time the medium is to be transferred from one virtual equipment element 50 to another. The computer unit executes the requested operation or calculation or simulation with the aid of a function. The static or dynamic parameters resulting from the calculation, for example a flow, a pressure or the like, can be communicated or transmitted to the user 13, for example in a log file. In particular, the simulation can also be visualized and "played" on the screen 11. In particular, the user 13 may change parameter entries of variable values of the parameter 300 and/or sensor 200 and/or process parameter datasets 400.

The user 13 can, for example, also select a process, for example a biochemical process, provided that this is stored together with the required model for calculation or simulation in at least one database for access. In particular, the user 13 can determine a process parameter 400 in one step. For example, photosynthesis of algae in a medium can be simulated. One or more of the following parameters of different parameter datasets can then be taken into account and/or calculated, among other things, in the simulation: Temperature (fluctuation), light incidence, volume of the medium, quantity of nutrients, light incidence, duration of the process, pressure and/or stirring speed, and the like. Some parameters can be fixed or invariable, whereas other parameters are flexible or variable. In particular, thermodynamically relevant processes are also simulated.

For example, by means of a "run button", the user 13 can cause the computer unit 10 to predict and/or simulate the desired process or operating status.

Figure 9:
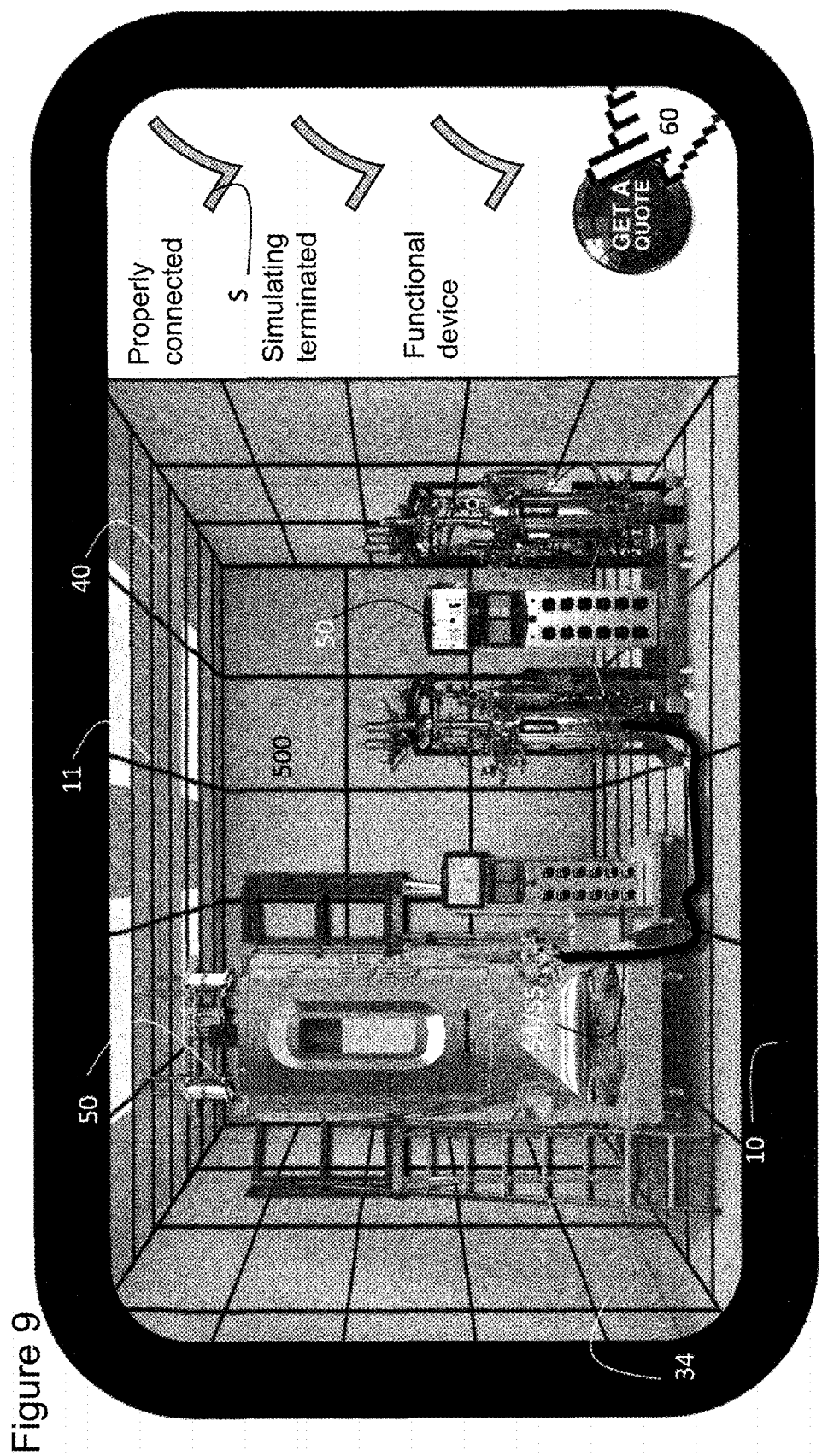
FIG. 9 is a step of predicting an operating status of at least a part of the equipment in accordance with one embodiment.

FIG. 9 illustrates the method step of a status message and the offer request 160, 170 in more detail in accordance with one embodiment. If all operating statuses are evaluated as harmless or correct on the basis of the prediction, i.e. if there is in particular no error message, the user 13 can be allowed to request an offer for the essential virtual or physical equipment elements 50. For example, a "get a quote" button can be provided so that a quote request can be made to one or more suppliers by clicking on it.

The computing unit 10 can process and/or forward the offer request directly. In a further step 180 an offer can be created. The user 13 may then decide whether to order the product, in particular one or more physical equipment elements 51 of the configured device 500 on the basis of the offer and/or the simulation results.

FIG. 10 shows a virtual environment 40 in accordance with an embodiment in which a virtual device 500 is located and/or positioned. The virtual environment 40 shows a map 52 of a physical equipment element 51 which is preferably identified by means of the sensor dataset 200 and is assigned to a virtual equipment element 50 (as well as preferably its parameter dataset 300). In other words, due to the sensor dataset 200, a physical equipment element 51 can be detected or identified and assigned to the virtual environment 40 as a virtual element. Further, in the virtual environment 40 another virtual equipment element 50 is arranged in the virtual environment 40. The virtual equipment element 50 is virtually connected to the virtual equipment element 50, which corresponds to the physical equipment element 51, by means of a virtual connection element 54 or a virtual hose 55.

The embodiment of the method for configuring equipment 500 by means of an augmented reality FIG. 10 comprises displaying a toolbar or toolbar t. The tool bar T allows the user 13 to cause the computer unit 10 to determine a tube length L of the virtual tube 55 ("calculate tube length"). The toolbar T shows further elements of a user interface UI, for example a control field for changing and/or determining parameter entries 300 with respect to the virtual hose 54 ("edit tube"). Furthermore, the user 13 can move the virtual tube 55 virtually over the virtual ground G by means of the tool bar element ("set tube to ground") and by means of the dynamic curvature adaptation ("adapt tube curvature"). In addition, the created configuration of the virtual equipment 500 may be reset (reset configuration) and/or saved ("save configuration").

FIG. 11 shows a user interface UI "in accordance with one embodiment. The user interface UI can be generated by an application and imaged on a screen 11. In one field, a virtual equipment element 50 is mapped for selection. By way of example, this is a virtual plastic container, in particular a virtual plastic disposable bag, which also has a virtual connection element 54 namely a virtual tube 55. Furthermore, an identity marking 62 in the form of a QR marking is mapped in accordance with a QR coding. For example, the identity marking 62 may be printed by the user 13 and positioned at a location in the physical environment 30 so that the computer unit 10 can map that identity marking 62 in the virtual environment 40 and arrange the corresponding virtual equipment element 50 virtually at the corresponding virtual location.

A parameter field P ("bag chamber") is further depicted remotely, on which one or more fields for entering and/or determining parameters, in particular a parameter dataset 300, are provided. For example, the user 13 may select a suitable virtual container under a field ("container of the bag") by clicking on it. The product or virtual furnishing element 50 "Palletank®" has already been selected, as indicated by the displayed hook and the completed field. Furthermore, a volume of "100 L" under the "Working Volume" field was also selected from the illustrated selection between 100 L, 200 L, 500 L and 1000 L. The parameters selected are part of a parameter dataset 300 by means of which the virtual container 50 shown is determined or characterized. The virtual container 50 corresponds in particular to a product, namely a physical furnishing element 51, which is available or which is distributed by the supplier. For example, the product may already exist, or the product may only be manufactured after configuration for the user 13.

In addition, a parameter field P "Flexsafe® 3D Bag for Palletank®" is shown on the user interface UI, within which further parameters of a parameter dataset 300 of the virtual bag named "Palletank" can be selected and/or determined. In this way, a user 13 can configure a virtual equipment element 50 before placing it in a virtual environment 40 with reference to one or more possible parameters.

FIG. 12 shows a user interface UI in accordance with one embodiment which has already been partly described in FIG. 11. The virtual bag or container 50 with ports x, as well as virtual connection elements 54, namely two virtual tubes 55 with virtual ports x each, are shown.

By means of the parameter field P named "Flexsafe® 3D Bag for Palletank®", the user 13 can determine that a virtual connection element 54 named "Aseptic Connector" can be configured. In the related parameter field P called "Tube material by application" the user can determine parameters such as material and length L of the virtual tube. For example, a length of "1500 mm (59")" from a range between 300 mm, 500 mm, 800 mm, 1000 mm, 1500 mm, 3000 mm and 5000 mm has already been selected or determined.

FIG. 13 shows a user interface UI in accordance with one embodiment which has already been partly described in FIGS. 11 and 12. In particular FIG. 13 illustrates how the user 13 adapts the depiction of the virtual equipment element 50, in particular the virtual tube 55, by means of the parameter determination. The user 13 has determined herein that the virtual tube 55 is intended to have a length L of "3000 mm (59")" instead of "1500 mm (59")". In the depiction of the virtual tube 55 in FIG. 13, it can be seen that the virtual tube appears correspondingly longer than in the depiction in FIG. 12. This method step of immediately adapting visually depicted virtual device elements 50 has the advantage that the user 13 can proceed particularly intuitively in the configuration of a device.

In general, a user 13 of the described method can be, for example, a customer or (potential) buyer who has interest in equipping his or her laboratory with devices or pieces of equipment comprising one or more physical equipment elements 51 which are offered in an online catalog or on a website of at least one supplier. The laboratory may, for example, already comprise one or more devices or physical equipment elements 51 which the supplier sells or has sold in the past. However, the laboratory can also be unequipped or empty and can be virtually equipped with virtual equipment elements 50.

A physical component may comprise a real physical component, such as a piece of furniture or a piece of laboratory equipment, in particular a table, chair, laboratory bench, hood, rack, shelf, tray, and/or physical equipment element 51, in particular one sold by a supplier. A real physical component can also comprise a port, in particular a gas and/or liquid discharge and/or supply, an outlet or a network access or supply, a light switch, a light, a ventilation, a window, a door and/or other infrastructure elements of a room. A computer unit 10 may be configured to map and identify a physical equipment element 51 and assign it to a corresponding virtual equipment element 50, which also substantially equivalent to transforming and/or digitizing a physical equipment element 51 into a virtual device element 50. In particular, a physical real component can thus be a registered physical, that is to say real, equipment element 51. A registered physical equipment element 51 is an equipment element which corresponds or is assigned to an entry in a table and/or a catalog and in particular to a parameter dataset 300. The entry preferably represents a physical equipment element 51 which can be ordered and purchased by a user and/or is and/or was offered for sale by a supplier. A component may also comprise a virtual component, in particular a virtual equipment element 50, for example an equipment element corresponding to an entry in a table and/or a catalog.

In particular, the method for configuring the equipment 500 may be particularly intuitive. Furthermore, the operator or user 13 can preferably be guided through process sequences for configuring a piece equipment 500 without the user needing or having to consult a manual for this purpose.

The computer unit 10 may comprise a microcontroller, a microprocessor and/or an integrated circuit configured to receive data from at least one sensor unit 20 and to transmit data to an output device, in particular a display 11. The computer unit 10 may be part of a computer system such as a PC, a smartphone 12 and/or a tablet 12. In particular, the computer unit 10 may comprise a computer unit of a device of the user 13 and the computer unit of a remote device, for example a supplier of goods. In other words, the computing power of a plurality of devices or units may be used to perform a calculation. The term computer unit 10 may in this case comprise the individual computing subunits.

All said virtual elements 50 are respectively arbitrarily simplified or arbitrarily complex models for physical real elements 51. The virtual elements 50 are determined by parameters (entries) of a parameter dataset 300 which have been determined or determined, among other things, using the corresponding physical equipment elements 51 and/or have been subsequently varied. Each virtual equipment element 50 can thus be used as a digital model of the physical equipment element 51. This does not mean, however, that the parameters that determine a virtual equipment element 50 also completely determine the parameters of a physical equipment element 51. The virtual equipment element 50 can also only serve as a simplified model in this respect. The parameters by which a virtual equipment element 50 and/or another virtual component is determined are kept in a dataset, for example a parameter 300 and/or a sensor 200 and/or a process parameter dataset 400.

The coded information content of a QR marking in accordance with a QR coding does not substantially correspond to the information content of an Augmented Reality AR marking. Nevertheless, a QR marking can serve as an AR marking because of its structural design, namely when only the sample but not the coding is analyzed.

In general, a common AR marking may also resemble a common QR marking in visual depiction, but typical AR markings usually have fewer black and white squares and are larger in size. It is not the purpose of an AR marking to transmit a string in accordance with a QR coding, whereas a QR marking transmits a string or corresponds to a string. A system based on the AR marking can recognize the position and orientation of the AR marking identified by a camera in 3D or derive it from the AR marking. In other words, an AR marking may comprise information, in particular two-dimensional patterns, which allow the position and orientation of the AR marking in the space thereof to be derived by analyzing the perspective depiction of the AR marking on an image.

The evaluation of a QR marking by means of a decryption of a QR coding and an AR marking is substantially very different. A value from a QR marking is read from black and white squares in accordance with a coding, but usually no position and orientation is read in this step. In contrast, an AR marking is identified from a group of known AR markings and at the same time their position and orientation are analyzed in real time. In particular, movements of an object provided with an AR marking can also be analyzed in this way.

AR marking are typically somewhat more accurate than QR markings and can be easily tracked by means of augmented reality systems. AR markings do not necessarily have to be read out or decrypted. An AR marking can also simply be detected or identified and a position and/or orientation can be derived from the position of the AR marking in space. In particular, movement of the AR marking can be tracked. On this basis, an interactive 3D animation and/or a virtual environment 40 with a virtual equipment element 50 can be played back accordingly and in real time. In particular, an augmented reality system is designed to manage without additional markings. This means that in the case it is not necessary for a user to have to provide a marking, which is referred to as "markerless tracking". However, this does not mean that there is no marking at all. Instead, existing features in a screen can serve as markings. For example, the logo of a company or an image on an object could serve as an AR marking which, without further action of the user, would be present anyway in the physical environment 30 as well as on the map of the physical environment 31. This could eliminate the need for additional (black and white) AR marking by the user.

REFERENCE NUMERALS

10 Computer unit
11 Screen
12 Smart device and/or smartphone and/or tablet
13 User
20 Sensor unit
21 Camera
30 Physical environment
31 Image or mapping of the physical environment
32 Raster and/or digitized 3D coordinates
33 Spatial marking, in particular gravitational direction or marking for indicating the gravitational direction
34 Real light source
35 Virtual light source
40 Virtual environment
50 Virtual equipment element
51 Physical equipment element
52 Mapping of physical equipment element
54 Virtual connection element
55 Virtual tube
56 Virtual adapter element
57 Proposed and/or presented selection of virtual equipment elements and/or catalog elements and/or product list and/or selection
58 End of a connection element
60 Mouse pointer
61 Object marking can be AR marking and/or QR marking
62 Identity marking can be AR marking and/or QR marking
100 Step of providing an augmented reality system
110 Step of recording a sensor dataset
120 Step of determining a virtual environment
130 Step of determining a virtual arrangement-select
131 Providing a product selection and/or a list of virtual equipment elements and selecting a virtual equipment element 132 Providing, identifying and assigning a physical equipment element
140 Step of determining a virtual arrangement—arrange
141 Automatic and/or manual arrangement of a virtual equipment element
142 Automatic arrangement
150 Step of predicting or meeting a prediction, in particular simulating a function and/or an operating status
160 Allowing an offer request and/or goods order request
170 Creating a offer
180 Creating a offer
200 Sensor dataset
300 Parameter
400 Process parameter dataset
500 Equipment
1000 Augmented reality system or system for generating an augmented reality
B Virtual ground in virtual environment
UI User interface
D Distance between virtual connections
L Length of a connection element
P Parameter field
S Status message
T Menu bar and/or toolbar
x Virtual port

The invention claimed is:

1. A method for virtually configuring a piece of equipment comprising:
providing an augmented reality system comprising a computer unit and at least one sensor unit;
detecting a sensor dataset associated with a physical environment by the at least one sensor unit;
determining a virtual environment based on the sensor dataset using the computer unit;
determining a virtual arrangement of at least one virtual and/or physical equipment element relative to the virtual environment, wherein the virtual and/or physical equipment element is assigned a respective parameter dataset; and
generating a prediction of functionality and/or operating status of at least one part of the equipment based on the parameter dataset and the sensor dataset,
wherein the at least one virtual equipment element includes at least one virtual connection element,
wherein determining the virtual arrangement comprises determining at least three virtual equipment elements, wherein one of the at least three virtual equipment elements corresponds to the virtual connection element;
wherein the parameter dataset associated with the virtual connection element comprises a length of the connection element; and
wherein two of the at least three virtual equipment elements each comprises at least one port for connecting a respective end of the virtual connection element;
and the method further comprises the following steps:
determining a virtual distance between at least two ports in the virtual environment based on the sensor dataset, the parameter dataset and a virtual location; and
determining a virtual length of the connection element based on the distance between at least two connections in the virtual environment, wherein the virtual length is an optimal length,
wherein, when determining the virtual length, the connection element in the virtual environment is arranged taking into account a detected gravitational direction.

2. The method of claim 1, wherein the at least one sensor unit comprises a 3D camera, and the step of detecting the sensor dataset associated with the physical environment further comprises a step of recording by means of the camera an image of the physical environment comprising spatial information or a gravitational direction.

3. The method of claim 2, further comprising a step of providing at least one spatial marking comprising a first AR marking, in the physical environment, wherein the spatial information is a 3D topology of the physical environment that is detected by means of the spatial marking.

4. The method of claim 3, comprising the step of providing an object marking comprising a second AR marking and/or a QR marking, in the physical environment,
wherein a virtual destination and/or a virtual orientation with respect to the virtual environment of the virtual equipment element and/or an identity of the virtual equipment element is identified and/or determined and/or specified by means of the object marking.

5. The method of claim 1, further comprising the following steps:
allowing a user and/or the computer unit of at least one virtual equipment element to be selected from a selection of a plurality of virtual equipment elements; and
providing a registered physical equipment element in the physical environment,
wherein the selecting of at least one virtual equipment element is performed by means of the computer unit and
wherein selecting at least one virtual equipment element is based on a step of identifying the registered physical equipment element with a virtual equipment element from the selection of the plurality of virtual equipment elements.

6. The method of claim 5, wherein the step of identifying the registered physical equipment element comprises a step of recognizing a shape feature of the physical equipment element and/or an identity marking comprising a third AR marking of the registered physical equipment element.

7. The method of claim 1, wherein the at least one virtual equipment element includes at least one of the following:
a bioreactor, a disposable bag, a container, a tank, a filter system, a mixing device, a fermentation tank, a centrifuge, a chromatography column, a membrane adsorber, a filling device; and/or the at least one virtual connection element includes, in particular at least one of the following:
an attachment, an adapter, a connection, a hose, a tube, a cable, a line, a tube, a pump; and
the parameter dataset comprises at least one variable and/or a fixed value from the following:
an identification coding, an order number, a volume, a length, a spatial extent, a diameter, a structure, a material, a range, an operating limit, compatibility with another virtual equipment element, compatibility with a biological and/or chemical reaction, a parameter to a medium and the biological and/or chemical reaction of the medium.

8. The method of claim 7, wherein determining the virtual arrangement comprises determining at least two virtual equipment elements, wherein one equipment element comprises a virtual connection element, and the method further comprises the steps of:
checking the compatibility between at least two virtual equipment elements;
wherein compatibility was found in the test:

allowing virtual connection of at least two virtual equipment elements by means of the virtual connection element by the user and/or the computer unit;
wherein compatibility was not detected in the test:
issuing an error message reporting the lack of compatibility.

9. The method of claim 1, wherein the augmented reality system further comprises a screen and the method further comprises a step of mapping the virtual environment and at least one virtual equipment element as an augmented reality map of the virtual arrangement on the screen.

10. The method of claim 9, wherein determining the virtual arrangement further comprises at least one step of dragging and dropping at least one virtual equipment element by means of the user and the screen.

11. The method of claim 9, wherein at least one variable value of the parameter dataset can be determined by the user on the screen.

12. The method of claim 11, wherein the at least one variable value of the parameter dataset is a length of the virtual equipment element, and wherein the screen is a touch screen and the length is determined by actuation of the touch screen.

13. The method of claim 1, wherein the sensor dataset associated with the physical environment comprises at least one of the following values: a temperature, a time, an electric field strength, a light intensity, a vibration, a noise.

14. The method of claim 1, wherein the step of predicting the operating status of at least part of the equipment comprises a step of simulating at least one dynamic definition of a dynamic value based on the sensor dataset, the parameter dataset and the virtual arrangement, the dynamic process comprising at least one of the following: a material flow, a biological process, a chemical process, a physical process, a mechanical process.

15. The method of claim 14, wherein the step of predicting an operating status comprises a step of reporting a correct operating status or reporting a faulty operating status, in particular based on the step of simulating the dynamic value.

16. The method of claim 1, further comprising the following steps:
allowing an offer request for at least one virtual equipment element based on the parameter dataset;
creating an offer based on the offer request;
allowing a goods order request; and
processing a goods order based on the goods order request.

17. The method of claim 1, comprising the step of manually marking in the virtual environment with the aid of a screen, in particular for marking a virtual spatial point and/or a virtual and/or physical equipment element.

18. A computer program product for a computer-aided virtual configuration of a piece of equipment, in particular bioprocessing equipment, wherein the computer program comprises computer-readable instructions which, when loaded and executed on a suitable computer unit, can carry out the following method steps:
determining a virtual environment based on a sensor dataset associated with a physical environment;
determining a virtual arrangement of at least one virtual equipment element relative to the virtual environment, wherein the virtual equipment element is assigned a respective parameter dataset; and
predicting a functionality and/or an operating status of at least one part of the equipment based on the parameter dataset and the sensor dataset,
wherein the at least one virtual equipment element includes at least one virtual connection element,
wherein determining the virtual arrangement comprises determining at least three virtual equipment elements, wherein one of the at least three virtual equipment elements corresponds to the virtual connection element;
wherein the parameter dataset associated with the virtual connection element comprises a length of the connection element; and
wherein two of the at least three virtual equipment elements each comprises at least one port for connecting a respective end of the virtual connection element;
and the method further comprises the following steps:
determining a virtual distance between at least two ports in the virtual environment based on the sensor dataset, the parameter dataset and a virtual location; and
determining the virtual length of the connection element based on the distance between at least two connections in the virtual environment, wherein the virtual length is an optimal length,
wherein, when determining the virtual length, the connection element in the virtual environment is arranged taking into account a detected gravitational direction.

19. An augmented reality system for virtually configuring a piece of equipment, in particular bioprocessing equipment, wherein the augmented reality system comprises:
at least one sensor unit adapted to detect a sensor dataset associated with a physical environment;
a computer unit configured to perform the following steps:
determining a virtual environment based on a sensor dataset associated with a physical environment;
determining a virtual arrangement of at least one virtual equipment element relative to the virtual environment, wherein the virtual equipment element is assigned a respective parameter dataset; and
predicting a functionality and/or an operating status of at least one part of the equipment based on the parameter dataset and the sensor dataset,
wherein the at least one virtual equipment element includes at least one virtual connection element,
wherein determining the virtual arrangement comprises determining at least three virtual equipment elements, wherein one of the at least three virtual equipment elements corresponds to the virtual connection element;
wherein the parameter dataset associated with the virtual connection element comprises a length of the connection element; and
wherein two of the at least three virtual equipment elements each comprises at least one port for connecting a respective end of the virtual connection element;
and the method further comprises the following steps:
determining a virtual distance between at least two ports in the virtual environment based on the sensor dataset, the parameter dataset and a virtual location; and
determining the virtual length of the connection element based on the distance between at least two connections in the virtual environment, wherein the virtual length is an optimal length, wherein, when determining the virtual length, the connection element in the virtual environment is arranged taking into account a detected gravitational direction.

* * * * *